(12) United States Patent
Ehrich et al.

(10) Patent No.: US 7,867,714 B2
(45) Date of Patent: Jan. 11, 2011

(54) TARGET-SPECIFIC COMPOMERS AND METHODS OF USE

(75) Inventors: Mathias Ehrich, San Diego, CA (US); Dirk Johannes Van den Boom, La Jolla, CA (US)

(73) Assignee: Sequenom, Inc., San Diego, CA (US)

( * ) Notice: Subject to any disclaimer, the term of this patent is extended or adjusted under 35 U.S.C. 154(b) by 0 days.

(21) Appl. No.: 12/489,164

(22) Filed: Jun. 22, 2009

(65) Prior Publication Data

US 2009/0258793 A1 Oct. 15, 2009

Related U.S. Application Data

(62) Division of application No. 10/874,898, filed on Jun. 23, 2004.

(51) Int. Cl.
| | |
|---|---|
| C12Q 1/68 | (2006.01) |
| C12P 19/34 | (2006.01) |
| C12M 1/34 | (2006.01) |
| C12M 3/00 | (2006.01) |
| C12N 15/00 | (2006.01) |
| C07H 21/02 | (2006.01) |
| C07H 21/04 | (2006.01) |

(52) U.S. Cl. .................. 435/6; 435/91.1; 435/287.2; 435/320.1; 536/23.1; 536/24.1; 536/24.3

(58) Field of Classification Search ................ 435/6, 435/91.2, 287.2, 320.1; 536/23.1, 24.1, 24.3
See application file for complete search history.

(56) References Cited

U.S. PATENT DOCUMENTS

| | | | |
|---|---|---|---|
| 5,149,797 A * | 9/1992 | Pederson et al. ........... 536/23.1 |
| 5,185,243 A | 2/1993 | Ullman et al. | |
| 5,356,774 A | 10/1994 | Axelrod et al. | |
| 6,027,889 A | 2/2000 | Baranay et al. | |
| 6,090,558 A | 7/2000 | Butler et al. | |
| 6,104,028 A | 8/2000 | Hunter et al. | |
| 6,111,251 A | 8/2000 | Hillenkamp | |
| 6,268,148 B1 | 7/2001 | Baranay et al. | |
| 6,312,892 B1 * | 11/2001 | Barany et al. ................. 435/6 |
| 6,322,970 B1 | 11/2001 | Little et al. | |
| 6,379,917 B1 | 4/2002 | Okun et al. | |
| 6,489,116 B2 * | 12/2002 | Wagner ........................ 435/6 |
| 6,506,594 B1 | 1/2003 | Baranay et al. | |
| 6,537,755 B1 | 3/2003 | Drmanac | |
| 6,589,485 B2 | 7/2003 | Koster | |
| 6,602,662 B1 | 8/2003 | Koster | |
| 6,635,452 B1 | 10/2003 | Monforte et al. | |
| 6,723,564 B2 | 4/2004 | Hillenkamp | |
| 6,797,470 B2 | 9/2004 | Baranay et al. | |
| 6,812,005 B2 | 11/2004 | Fan et al. | |
| 6,858,412 B2 | 2/2005 | Willis et al. | |
| 6,890,741 B2 | 5/2005 | Fan et al. | |
| 6,955,901 B2 | 10/2005 | Schouten | |
| 2002/0006617 A1 | 1/2002 | Fan et al. | |
| 2003/0033091 A1 | 2/2003 | Opalsky | |
| 2003/0036064 A1 | 2/2003 | Stuelpnagel et al. | |
| 2003/0104434 A1 | 6/2003 | Fan et al. | |
| 2003/0108900 A1 | 6/2003 | Oliphant et al. | |
| 2003/0119004 A1 * | 6/2003 | Wenz et al. ................ 435/6 |
| 2003/0170684 A1 | 9/2003 | Fan | |
| 2003/0175772 A1 * | 9/2003 | Wang ........................... 435/6 |
| 2003/0211489 A1 | 11/2003 | Shen et al. | |
| 2004/0121364 A1 | 6/2004 | Chee et al. | |
| 2004/0224352 A1 | 11/2004 | Fan et al. | |
| 2005/0026180 A1 | 2/2005 | Willis et al. | |
| 2005/0287533 A1 | 12/2005 | Ehrich | |
| 2006/0088826 A1 | 4/2006 | Van Eijk et al. | |

FOREIGN PATENT DOCUMENTS

| | | |
|---|---|---|
| DE | 42 13 029 | 4/1993 |
| WO | WO 00/66771 | 9/2000 |
| WO | WO 2004/503839 | 6/2004 |
| WO | WO03060163 | 7/2004 |

OTHER PUBLICATIONS

Tang et al, Single nucleotide polymorphism analyses by MALD-TOF MS, 2003, International Journal of Mass Spectrometry, 226, 37-54.*
Barany, F., "Genetic disease detection and DNA amplification using cloned thermostable ligase," PNAS, Jan. 1, 1991;88(1):189-93.

(Continued)

Primary Examiner—Stephen Kapushoc
Assistant Examiner—Narayan K Bhat
(74) Attorney, Agent, or Firm—Grant Anderson, LLP

(57) ABSTRACT

Provided herein are libraries of nucleic acid species each comprising a transcription unit having a promoter region operatively linked to a coding sequence. The coding sequence of each nucleic acid species encodes a RNA cleavage substrate comprising a unique compomer species and a cleavage site. Each compomer species has a molecular mass distinguishable from the molecular mass of other compomer species in the library, and cleavage at a cleavage site releases a polynucleotide comprising the compomer species from the RNA cleavage substrate.

12 Claims, 13 Drawing Sheets

OTHER PUBLICATIONS

Gille, et al., "Genomics deletions of MSH2 and MLH1 in colorectal cancer families detected by a novel mutation detection approach," British Journal of Cancer 2002, 87, 892-897.

Higuchi, et al., "Kinetic PCR Analysis:Real-time Monitoring of DNA Amplification Reactions," Bio/Technology Sep. 1993, vol. 11, 1026-1030.

International Search Report and Written Opinion mailed: Jun. 26, 2008, for PCT/US05/22004 filed: Jun. 22, 2005.

Lizardi, et al., "Exponential amplification of recombinant RNA hybridization probes," Biotechnology, Oct. 6, 1988(10), 1197-1202.

Nakagawa, et al., "Identification and characterization of Genomic Rearrangements of MSH2 and MLH1 in Lynch Syndrome (HNPCC) by Novel Techniques," Human Mutation, Mutation in Brief #642 2003, 1-6.

Newton, et al., "Perspectives in PCR," BIOS Scientific Publishers, 1994 pp. 191.

Office Action mailed on: Jul. 17, 2009 for U.S. Appl. No. 10/874,898, filed Jun. 23, 2004 and published as:US 2005-0287533 A1 on:Dec. 29, 2005, Enrich, et al.

Office Action mailed on: Mar. 19, 2008 for U.S. Appl. No. 10/874,898, filed Jun. 23, 2004 and published as:US 2005-0287533 A1 on:Dec. 29, 2005, Enrich, et al.

Office Action mailed on: Jun. 11, 2007 for U.S. Appl. No. 10/874,898, filed Jun. 23, 2004 and published as:US 2005-0287533 A1 on:Dec. 29, 2005, Enrich, et al.

Office Action mailed on: Jul. 17, 2009 for U.S. Appl. No. 10/874,898, filed Jun. 23, 2004 and published as:US 2005-0287533 A1 on:Dec. 29, 2005, Enrich, et al.

Sambrook, "Synthetic Oligonucleotide Probes," Molecular Cloning: A Laboratory Manual; 2nd, Ed., Chapter 11, Cold Spring Harbor Laboratory Press, New York, 1989.

Schouten, et al., "Relative quantification of 40 nucleic acid sequences by Multiplex ligation-dependent probe amplification," Nucleic Acids Res. 2002, vol. 30, No. 12e57, pp. 1-13.

Tang et al., "Single nucleotide polymorphism analysis by MALDI-TOF MS", 2003, International Journal of Mass Spectrometry, 226, 37-54.

van Eijk, et al., "SNPWave: a flexible multiplexed SNP genotyping technology," Nucleic Acids Res., Mar. 5, 2004; vol. 32, No. 4, 1-13.

Walker, et al., "Multiplex strand displacement amplification (SDA) and detection of DNA sequences from Mycobacterium tuberculosis and other mycobacteria," Nucleic Acids Res. Jul. 11, 1994;22(13):2670-7.

Hartmern et al., RNase T1 mediated base-specific cleavage and MALDI-TOF MS for high-throughput comparative sequence analysis, Nucleic Acids Research, Oxford University Press, Surrey, GB, vol. 31, No. 9, May 1, 2003.

Krebs et al., "RNAseCut: a MALDT mass spectrometry-based method for SNP discovery," Nucleic Acids Research, Oxford University Press, Surrey, GB, vol. 31, No. 7, Apr. 1, 2003.

Rodi et al., "A Strategy for the Rapid Discovery of Disease Markers Using the MassArray System", Biotechniques, Informa Life Sciences Publishing, Westborolugh, MA, USA, vol. 32, No. Suppl, Jun. 1, 2002.

Supplemental European Search Report mailed on Sep. 29, 2009 in European Application EP 05857471 filed on Jun. 22, 2005.

Office Action mailed on: Apr. 23, 2010 for U.S. Appl. No. 10/874,898, filed Jun. 23, 2004 and published as:US 2005-0287533 A1 on: Dec. 29, 2005.

Office Action mailed on: Apr. 23, 2010 for U.S. Appl. No. 10/874,898, filed Jun. 23, 2004 and published as:US 2005-0287533 A1 on: Dec. 29, 2005.

\* cited by examiner

Figure 1
Target Detection Reagent Schematic
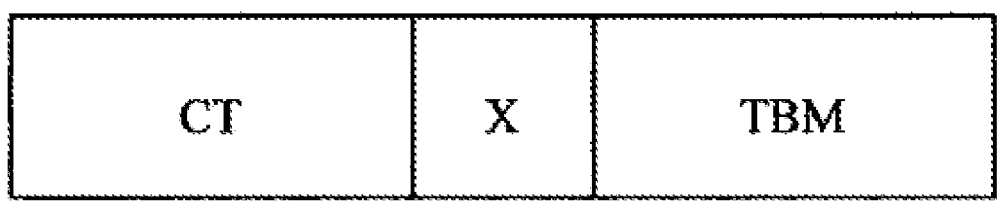
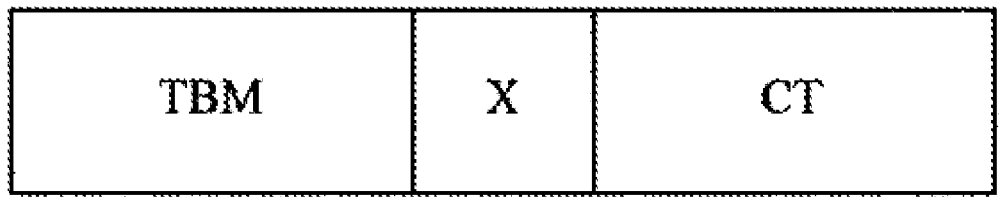
CT = compomer template
TBM = target binding moiety
X = direct CT-TBM linkage
or
a linker

Figure 2

Compomer Template Schematic

| Compomer-Encoding Region | Terminator |
|---|---|

Compomer-Encoding Region

1. Contains one or more nucleobase-containing moieties; and
2. Serves as a template for generating compomers (*e.g.*, by enzymatic processes (*e.g.*, PCR, TMA, *etc.*) or other suitable chemistry)

Terminator

1. Allows compomer terminus to be defined. Examples include additional nucleobase subunits, at least one of which serves as a cleavage base, a chain-terminating base (*e.g.*, a ddNTP), etc.

Figure 3

Compomer Template Schematic (2)

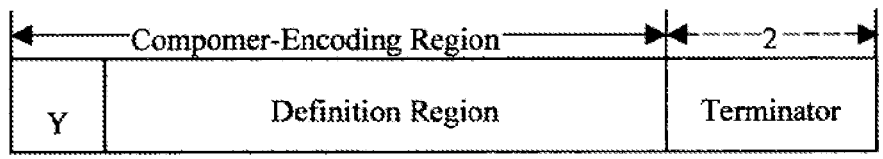

Compomer-Encoding Region

Y = 1. Nothing; or
    2. One or more nucleobase subunits – if present, common to all members of library.

Definition Region – One or more nucleobase subunits serve as the template for that portion of compomer species that differ from other members of the particular compomer library.

Terminator

1. Nothing; or
2. One or more additional nucleobase subunits, including a cleavage base (note: cleavage can occur in the nucleobase, the scaffold, or an intersubunit linkage and /or a chain terminating subunit (*e.g.*, a ddNTP); and
3. Preferably common to members of the particular compomer library encoded by the compomer templates.

Figure 4

Compomer Template Schematic

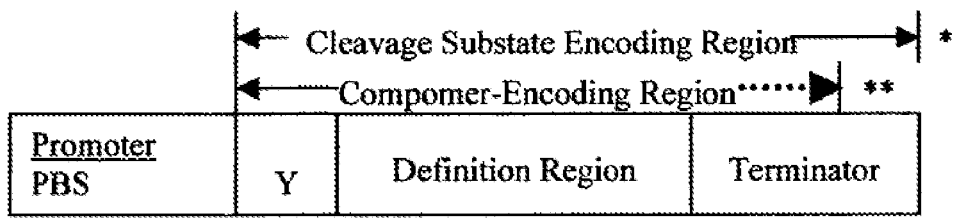

Promoter – encodes promoter

PBS – Primer Binding Site – encodes site for binding primer used for primer extension Y = nothing or one or more nucleobase subunits that serve as a template for subunits incorporated into the encoded compomer or cleavage substrate. Note: if used in a given compomer template, the Y region preferably is common (i.e., is the same) among the compomer templates and encoded compomers (or cleavage substrates).

Definition Region – as in Figure 3

Terminator – as in Figure 3

\* - Indicates that CT (compomer template) codes for a cleavage substrate that includes at least one additional nucleobase subunit as compared to the included compomer.

\*\* - (••••) indicates that CT codes for chain terminating nucleobase subunit

Figure 5

Compomer Schematic

| Y | Definition Region | Terminator |
|---|---|---|

Y (1) Nothing; or
(2) One or more subunits, preferably common to all compomers in the given compomer library.

Terminator (1) Nothing; or
(2) For example, a chain-terminating subunit (or portion thereof).

Definition Region

One or more subunits (*e.g.*, nucleobase – containing subunits, amino acid subunits, sugar subunits, *etc.*)
Example: $[A_xC_yG_z]_K$
$x = 0\text{-}5$
$y = 0\text{-}10$
$z = 0\text{-}10$
$K = 1\text{-}5$

Figure 6

Assembly of a Target Detection Reagent library from a single Compomer Template library and two Target Binding Moiety libraries, one for targeting nucleic acids, the other for targeting polypeptides

| CT Library | TBM Library 1 (targets = nucleic acids) | TBM Library 2 (targets = polypeptides) |
|---|---|---|
| CT1 | TBM1$_1$ | TBM2$_1$ |
| CT2 | TBM1$_2$ | TBM2$_2$ |
| CT3 | TBM1$_3$ | TBM2$_3$ |
| ⋮ | ⋮ | ⋮ |
| CT$_n$ | TBM1$_x$ | TBM2$_y$ |

1. Elect to detect target molecules targeted by TBM1$_2$, TBM1$_3$, TBM1$_{20}$, TBM1$_{17}$ and TBM2$_5$, for a total of 5 target molecules.
2. Elect which CT(s) to use, prefer to achieve sufficiently large differences between the defined characteristic(s) of the 5 encoded compomer species. Here, compomer species CT1-5 are selected.
3. Determine whether to use a linker between each CT and TBM in a given target detection reagent.
4. Assemble (or directly synthesize) target detection reagents to yield the following target detection reagents:

| | |
|---|---|
| CT1 | TBM1$_2$ |
| CT2 | TBM1$_3$ |
| CT3 | TBM1$_{17}$ |
| CT4 | TBM1$_{20}$ |
| CT5 | TBM2$_5$ |

Figure 7

Representative Compomer Template Schematics:

| T7 promoter | GGG | $[A_xC_yG_z]_k$ | U |

| T7 promoter | GGG | $[A_xT_yG_z]_k$ | C |

| T7 promoter | GGG | $[A_xC^{me}_yU_z]_k$ | G |

| SP6 promoter | GAA | $[A_xC_yG_z]_k$ | T |

| SP6 promoter | GAA | $[A_xT_yG_z]_k$ | C |

| SP6 promoter | GAA | $[A_xC^{me}_yU_z]_k$ | G |

↓ promoter
↓ start codon
↓ compomer specificity region
↓ cleavage base

Figure 9B

Representative Compomer Library

| Compomer Base Composition | Length (in bases, after cleavage) | mass_natural (Daltons) |
|---|---|---|
| (rA7 rG0) rC | 7 | 2609.65 |
| (rA3 rG4) rC | 7 | 2673.65 |
| (rA8 rG0) rC | 8 | 2938.86 |
| (rA4 rG4) rC | 8 | 3002.86 |
| (rA0 rG8) rC | 8 | 3066.86 |
| (rA9 rG0) rC | 9 | 3268.07 |
| (rA5 rG4) rC | 9 | 3332.07 |
| (rA1 rG8) rC | 9 | 3396.07 |
| (rA0 rG11) rC | 11 | 4102.48 |
| (rA6 rG6) rC | 12 | 4351.7 |
| (rA0 rG12) rC | 12 | 4447.69 |
| (rA13 rG1) rC | 14 | 4930.12 |
| (rA6 rG8) rC | 14 | 5042.12 |
| (rA1 rG13) rC | 14 | 5122.11 |
| (rA15 rG0) rC | 15 | 5243.33 |
| (rA11 rG4) rC | 15 | 5307.33 |
| (rA7 rG8) rC | 15 | 5371.33 |
| (rA3 rG12) rC | 15 | 5435.32 |
| (rA16 rG0) rC | 16 | 5572.54 |
| (rA12 rG4) rC | 16 | 5636.54 |
| (rA8 rG8) rC | 16 | 5700.53 |
| (rA4 rG12) rC | 16 | 5764.53 |
| (rA0 rG16) rC | 16 | 5828.53 |
| (rA17 rG0) rC | 17 | 5901.75 |
| (rA13 rG4) rC | 17 | 5965.75 |
| (rA9 rG8) rC | 17 | 6029.74 |
| (rA5 rG12) rC | 17 | 6093.74 |
| (rA1 rG16) rC | 17 | 6157.74 |
| (rA18 rG0) rC | 18 | 6230.96 |
| (rA14 rG4) rC | 18 | 6294.96 |
| (rA10 rG8) rC | 18 | 6358.95 |
| (rA6 rG12) rC | 18 | 6422.95 |
| (rA2 rG16) rC | 18 | 6486.95 |
| (rA19 rG0) rC | 19 | 6560.17 |
| (rA15 rG4) rC | 19 | 6624.17 |
| (rA11 rG8) rC | 19 | 6688.16 |

Figure 9B (continued)

| | | |
|---|---|---|
| (rA7 rG12) rC | 19 | 6752.16 |
| (rA3 rG16) rC | 19 | 6816.16 |
| (rA20 rG0) rC | 20 | 6889.38 |
| (rA16 rG4) rC | 20 | 6953.38 |
| (rA12 rG8) rC | 20 | 7017.37 |
| (rA8 rG12) rC | 20 | 7081.37 |
| (rA4 rG16) rC | 20 | 7145.37 |
| (rA0 rG20) rC | 20 | 7209.37 |
| (rA18 rG3) rC | 21 | 7266.59 |
| (rA14 rG7) rC | 21 | 7330.58 |
| (rA10 rG11) rC | 21 | 7394.58 |
| (rA6 rG15) rC | 21 | 7458.58 |
| (rA2 rG19) rC | 21 | 7522.58 |
| (rA20 rG2) rC | 22 | 7579.8 |
| (rA16 rG6) rC | 22 | 7643.79 |
| (rA12 rG10) rC | 22 | 7707.79 |
| (rA8 rG14) rC | 22 | 7771.79 |
| (rA4 rG18) rC | 22 | 7835.79 |
| (rA22 rG1) rC | 23 | 7893.01 |
| (rA18 rG5) rC | 23 | 7957.01 |
| (rA14 rG9) rC | 23 | 8021 |
| (rA9 rG14) rC | 23 | 8101 |
| (rA5 rG18) rC | 23 | 8165 |
| (rA22 rG2) rC | 24 | 8238.22 |
| (rA18 rG6) rC | 24 | 8302.21 |
| (rA14 rG10) rC | 24 | 8366.21 |
| (rA8 rG16) rC | 24 | 8462.21 |
| (rA4 rG20) rC | 24 | 8526.2 |
| (rA22 rG3) rC | 25 | 8583.43 |
| (rA17 rG8) rC | 25 | 8663.42 |
| (rA12 rG13) rC | 25 | 8743.42 |
| (rA8 rG17) rC | 25 | 8807.42 |
| (rA26 rG0) rC | 26 | 8864.64 |
| (rA22 rG4) rC | 26 | 8928.64 |
| (rA18 rG8) rC | 26 | 8992.63 |
| (rA14 rG12) rC | 26 | 9056.63 |
| (rA7 rG19) rC | 26 | 9168.62 |
| (rA25 rG2) rC | 27 | 9225.85 |
| (rA21 rG6) rC | 27 | 9289.84 |
| (rA17 rG10) rC | 27 | 9353.84 |
| (rA13 rG14) rC | 27 | 9417.84 |
| (rA9 rG18) rC | 27 | 9481.84 |
| (rA5 rG22) rC | 27 | 9545.83 |
| (rA1 rG26) rC | 27 | 9609.83 |
| (rA17 rG11) rC | 28 | 9699.05 |

| | | |
|---|---|---|
| (rA13 rG15) rC | 28 | 9763.05 |
| (rA9 rG19) rC | 28 | 9827.04 |
| (rA3 rG25) rC | 28 | 9923.04 |
| (rA20 rG9) rC | 29 | 9996.26 |

Figure 9B (continued)

Figure 10
Target Detection Reagent
Target Binding Moiety = antibody
A 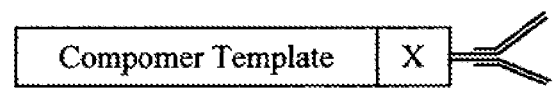
B 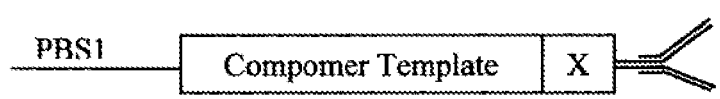
C 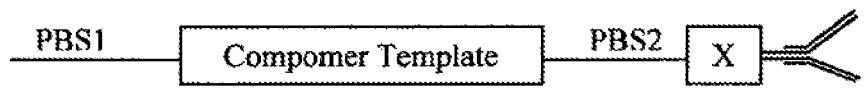
PBS = Primer binding site

TARGET-SPECIFIC COMPOMERS AND METHODS OF USE

This patent application is a divisional application of U.S. patent application Ser. No. 10/874,898 filed on Jun. 23, 2004, entitled Target-Specific Compomers and Methods of Use, naming Mathias Ehrich and Dirk Johannes Van den Boom as inventors. Subject matter of each of the foregoing patent application is herein incorporated by reference in its entirety.

FIELD OF THE INVENTION

The present invention generally relates to the field of chemical analysis and concerns compositions and methods for detecting particular target biomolecules, including nucleic acid molecules. In particular, the invention relates to compositions and methods that enable the indirect detection and analysis of particular biomolecules, for example, by mass spectrometry.

BACKGROUND OF THE INVENTION

1. Introduction

The following description includes information that may be useful in understanding the present invention. It is not an admission that any such information is prior art, or relevant, to the presently claimed inventions, or that any publication specifically or implicitly referenced is prior art.

2. Background

Efficient, high fidelity detection and analysis of biomolecules (e.g., nucleic acids, proteins, carbohydrates, and lipids) represent a major challenge in biology. These challenges are particularly acute in the context of the analyzing biological samples, which by their nature are extremely complex, both in terms of the number of different molecular species present, as well as with regard to the numbers of molecules of the various particular species. Due to this complexity, extremely sensitive and selective methods are required in order to generate valid, reproducible results. Further complicating matters is the need to achieve such results in a commercially viable way, e.g., in terms of cost, time, etc.

The importance of adequately addressing these challenges is perhaps best considered in the context of the large-scale detection and analysis of nucleic acids, which store the genetic information of all living organisms (e.g., animals, plants, and microorganisms). Briefly, genetic information is generally encoded in deoxyribonucleic acid (DNA), although certain viruses comprise genomes made of ribonucleic acid (RNA). In humans, a complete haploid genome comprises about three billion nucleotides, and contains about 35,000 genes spread across 24 chromosomes (twenty two somatic chromosomes and two sex chromosomes). Naturally occurring DNA and RNA molecules are enzymatically synthesized as linear polymers of nucleotides, which differ from each other only in terms of the bases included particular nucleotides. In DNA, four different deoxyribonucleotides are found, designated "A", "G", "C", and "T" due to the inclusion of an adenine, guanine, cytosine, or thymine base in the particular deoxyribonucleotide. Similarly, RNA is comprised of four different ribonucleotides, designated "A", "G", "C", and "U" due to the inclusion of either an adenine, guanine, cytosine, or uracil base in the nucleotide. In nature, genomic DNA is typically double-stranded, with one DNA strand being hybridized to the other in an anti-parallel fashion according to canonical Watson-Crick base pairing, where the A's on one strand always hydrogen bond with T's on the other strand, and G's always pair with C's. The same base-pairing rules apply with RNA, except that in RNA, U replaces T and thus pairs with A (in either DNA or RNA).

In nature, the nucleotide sequence of a particular nucleic acid is not random, and it is the particular sequence of nucleotides that distinguishes one member of a species from another member of the same species, as well as one gene from another. Generally, each gene codes for a specific protein, although some genes ultimately encode several proteins due to differential splicing of messenger RNAs transcribed from the same gene. In any event, after a protein-encoding gene is expressed by transcription and translation, the encoded protein fulfills a specific function within a living cell.

It is known that for a given gene, or genetic locus, one or more different alleles may exist. Alleles for a given gene differ from one another by differences in the nucleotide sequence of each allele. Alleles of a given gene may arise from a substitution of one nucleotide for another at a given nucleotide position. Alternatively, allelic differences may be due to the insertion or deletion of one or more nucleotides in the different alleles. As a result of such differences in protein-encoding regions of a gene, the proteins encoded by the different alleles may differ in size and/or amino acid sequence. With regard to proteins that are enzymes, differences in amino acid sequence can result in differences in catalytic rates, substrate specificity, co-factor requirements, cellular localization, stability, pH optimums, etc., some or all of which may be relevant, for example, in the context of disease detection, prevention, and treatment (e.g., the suitability of administering a particular drug to a particular patient drug/protein interactions). On the other hand, if the difference(s) between alleles is(are) due to changes in a regulatory region of the gene, the level of expression of the proteins encoded by the particular alleles may differ, even markedly.

Changes in the nucleotide sequence of a genomic nucleic acid molecule occur as a result of mutations, where during replication copying of a template nucleic acid does not result in exact duplication of the template nucleic acid. Mutations can also occur during DNA repair, such that one or both strands of a DNA duplex differs in nucleotide sequence when compared before and after a repair reaction. As mentioned above, mutations during replication or repair include the deletion, insertion, and/or substitution of one or more nucleotides in one or both strands of a double-stranded DNA. Mutations that involve a substitution of one nucleotide for another (e.g., A for G) are termed "point mutations" since they occur at a particular nucleotide position. In protein coding regions, a point mutation can be a "missense" mutation, which results in a change in the amino acid encoded by the particular codon in which the mutation occurred; a "nonsense" mutation, where the change results in the codon changing from one that encodes an amino acid to one that codes for a stop codon and thereby leads to a truncated protein; or a silent mutation, which results in the codon coding for the same amino acid as before. Again, mutations can also occur in non-coding regions, as well. While such mutations do not alter the amino acid sequence of the protein encoded by the gene, they may affect regulation of the expression of the gene, the stability of the DNA or RNA molecule, etc.

Whether a particular mutation persists over time in the gene pool is determined by the process of natural selection, where changes that, over time, improve reproductive fitness survive, and those that do not disappear. Regardless of evolutionary effects and as noted above, mutations can result in proteins with altered, or, in some cases, even lost biochemical activities, which, in turn, can cause disease, an adverse reaction to a particular drug, etc. Similarly, mutations can cause aberrant regulation of gene expression, which can also lead to disease, altered drug sensitivity, etc. due the relative over- or under-abundance of one or more particular gene products.

Diseases caused by mutation, whether inherited or originating in the DNA of a particular subject, are said to be "genetic diseases" or the like. More than 4,000 genetic diseases are currently known to result from allelic differences, including hemophilias, thalassemias, Duchenne Muscular Dystrophy (DMD), Huntington's Disease (HD), Alzheimer's Disease, Cystic Fibrosis (CF), and sickle cell anemia. In addition to diseases caused by mutation that give rise a disease-associated alleles, genetic diseases can also be caused by larger genetic abnormalities, such as translocations, duplications, and deletions of some or all of a particular chromosome. Examples of such abnormalities include Trisomy 21 (the cause of Down's Syndrome), Trisomy 13 (which causes Patau Syndrome), Trisomy 18 (which causes Edward's Syndrome), Monosomy X (the cause of Turner's Syndrome), and other sex chromosome aneuploidies such as XXY (which causes Klinefelter's Syndrome). Further, it is known that certain DNA sequences predispose an individual to any of a number of diseases, such as diabetes, arteriosclerosis, obesity, various autoimmune diseases, and cancer (e.g., colorectal, breast, ovarian, lung, and prostate cancer), and as well can predict how a patient will respond to a particular drug (i.e., will s/he respond at all, and, if so, will the response be a positive or adverse reaction?). Genetic differences also have relevance in the area of organ and tissue transplantation, as a failure to "match" HLA (human leukocyte antigen) types can lead to organ or tissue rejection. Due to the genetic variation between individuals within a given species, DNA sequences can also serve as "fingerprints" to detect or identity different individuals, assess paternity or other aspects of relatedness among members of a species, etc.

Given the growing importance of nucleic acid analysis in a variety of fields, several methods for detecting and characterizing DNA have been developed. For example, nucleic acid sequences can be identified by comparing by gel electrophoresis the mobility of an amplified nucleic acid fragment with a known standard or by hybridization with a probe oligonucleotide that is complementary to the sequence to be identified. Detection, however, can only be accomplished if the nucleic acid fragment is labeled with a sensitive reporter function (e.g., a molecule that includes a radioactive isotope (e.g., $^3$H, $^{32}$P, or $^{35}$S) or that is fluorescent or chemiluminescent). Radioactive labels, however, can be hazardous, the signals they produce decay over time, and they require special disposal procedures. Non-isotopic labels (e.g., fluorescent labels) typically suffer from a lack of sensitivity and fading, particularly when high intensity lasers are used. Additionally, procedures that involve labeling, electrophoresis, and subsequent detection are laborious, time-consuming, and error-prone.

Mass spectrometry, on the other hand, allows individual molecules (e.g., nucleic acids, peptides, and proteins) to be "weighed" by ionizing the molecules in vacuo and making them "fly" by volatilization. Under the influence of combinations of electric and magnetic fields, the ions follow trajectories depending on their individual mass (m) and charge (z). Mass spectrometry has long been part of the routine physical-organic repertoire for analysis and characterization of low molecular weight organic molecules. Due to the analytical advantages of mass spectrometry in providing high detection sensitivity, accuracy of mass measurements, detailed structural information, and speed, as well as on-line data transfer to a computer, considerable effort has been devoted to the use of mass spectrometry for the structural analysis of nucleic acids.

See, e.g., U.S. Pat. Nos. 6,706,530; 6,635,452; 6,602,662; 6,589,485; 6,569,385; 6,566,055; 6,558,902; 6,468,748; 6,436,635; 6,428,955; 6,300,076; 6,277,573; 6,268,144; 6,268,131; 6,258,538; 6,235,478; and 6,225,450. Today, advanced techniques for the ionization/desorption of samples containing large biomolecules such as polynucleotides have been developed, including electrospray/ionspray, and particularly, matrix-assisted laser desorption/ionization (MALDI). MALDI mass spectrometry typically uses a time-of-flight (TOF) configuration to analyze mass.

Another key advantage offered by mass spectrometry is that it provides a great ability to multiplex, i.e., it allows for many different molecules to be specifically and sensitively distinguished in a single analysis. Recently, systems that employ nonvolatile releasable tag molecules that contain releasable mass labels have been described. See, e.g., U.S. Pat. No. 6,635,452. In such systems, one or more detectable, nonvolatile mass label each specific for a particular target nucleic acid are released from probe molecules that specifically hybridize to particular nucleotide sequences. Mass spectrometry-based detection of a particular mass label thus provides indirect detection of the target molecule correlated with the particular mass label. Because of the sensitivity afforded by mass spectrometry, tens, hundreds, and even thousands of different probe species, each having a different releasable mass label, can be used in a single multiplexed reaction. Such systems, however, require the release of the detectable, nonvolatile mass labels from the probes. Thus, there remains the opportunity to develop other, perhaps even more efficient systems that allow for the simultaneous detection of a large number of different target biomolecules (e.g., nucleic acid molecules and/or proteins) in a biological sample. This will allow for the systematic, large-scale analysis of multiple target molecules with predetermined properties and/or functions.

3. Definitions

Before describing the instant invention in detail, several terms used in the context of the present invention will be defined. In addition to these terms, others are defined elsewhere in the specification, as necessary. Unless otherwise expressly defined herein, terms of art used in this specification will have their art-recognized meanings.

The term "allele" or "allelic variant" refers to alternative forms of a particular gene, and thus occupy the same locus or position on homologous chromosomes or extrachromosomal DNA. When a subject having a diploid genome has two identical alleles of a gene, the subject is said to be homozygous for the gene or allele. When a subject has two different alleles of a gene, the subject is said to be heterozygous for the gene. Alleles of a specific gene can differ from each other by one or more nucleotides, either or both in terms of number of nucleotides and/or nucleotide identity as specific nucleotide positions as a result of, for example, nucleotide substitutions, deletions, and/or insertions. Thus, an allele can also be a mutant form of a gene.

The term "amino acid" refers to naturally occurring and non-naturally occurring amino acids, as well as any modified amino acid that may be synthesized or, alternatively, obtained from a natural source.

An "amplicon" is a nucleic acid molecule generated in a nucleic acid amplification reaction, and which is derived from a target nucleic acid. An amplicon contains a target nucleic acid sequence that may be of the same or opposite sense as the target nucleic acid. An amplicon can also contain sequences not present in the nucleic acids from which the amplicon was derived.

An "amplification primer" or "primer" means an oligonucleotide capable of hybridizing to a primer binding site (i.e., a sequence of nucleobases complementary to the base sequence of the primer) and acting as a primer and/or a promoter template (e.g., for synthesis of a complementary strand, thereby forming a functional promoter sequence) for the initiation of nucleic acid synthesis. If the primer is designed to also encode a sequence to initiate RNA synthesis (e.g., a promoter), it is termed a "promoter-primer," and it preferably contains, in addition to a region for hybridizing to a primer binding site, a base sequence that is non-complementary to the target nucleic acid but which is recognized by an RNA polymerase, such as a T7, T3, or SP6 RNA polymerase. An amplification primer may contain a 3' terminus that is modified to prevent or lessen the rate or amount of primer extension (see, e.g., U.S. Pat. No. 5,766,849). Preferably, two or more different primers are used in amplification processes. A "universal" primer refers to a primer designed to hybridize to a primer binding site that is independent of the sequence to be amplified. As a result, universal primers are particularly useful in multiplex amplification reactions, wherein a number different target sequences can be amplified using a single pair of universal primers.

The terms "biological sample" refers to material obtained from any living (or formerly living) source (e.g., human, animal (e.g., mammals such as bovine, canine, equine, feline, ovine, and porcine animals, fish, birds, etc.), plant, bacteria, fungi, protist, or virus) and which contains one or more nucleic acids and/or populations of other target biomolecules. Biological samples can be made of solid materials (e.g., tissue, cell pellets, biopsies, etc.), or biological fluids (e.g., urine, blood, saliva, amniotic fluid, mouth wash, lymph, sweat, sputum, mucous, tears, etc.). Biological samples represent a sub-genus of "samples", which can be any sample of material containing one or more target molecules that can be detected and/or analyzed using one or more target detection reagents according to the invention.

A "biomolecule" refers to a molecule that occurs naturally in a biological system (e.g., an organism). Representative classes of biomolecules include nucleic acids, proteins, peptides, antibodies, enzymes, carbohydrates, lipids, metals, and toxins. A "target" biomolecule is a biomolecule targeted by a target detection reagent of the invention.

The term "coding region" of a compomer template refers to a region that encodes a compomer or a cleavage substrate, as the case may be.

Two single stranded nucleic acid molecules are "complementary" when over at least a portion of their respective lengths there is a region of sufficient size (i.e., a number of nucleobase subunits, e.g., nucleotides) to allow sufficient hydrogen bonding between the two nucleic acids to stabilize a duplex formed by hybridization of the two nucleic acids. Thus, for the purpose of this invention, a first nucleic acid is deemed to be perfectly complementary to a second nucleic acid when each base in the first polynucleotide is paired with a complementary base in the second polynucleotide over the region of intended complementarity, which can include all or only a portion of either or both of the two nucleic acid molecules. As will be appreciated, two single-stranded nucleic acid molecules can also be less than perfectly complementary over the region of intended complementarity and still exhibit sufficient complementarity to allow hybridization between the nucleic acids under stringent hybridization conditions.

"Complement" is used as a synonym for a nucleic acid that is complementary to another nucleic acid.

A "compomer" is molecule synthesized in a target detection assay from a compomer template to indirectly indicate the presence of a particular target molecule in a sample being assayed. Compomers are comprised of one or more subunits. Particularly preferred subunits for compomer polymerization are nucleobase subunits.

A "compomer template" refers to that portion of a target detection reagent of the invention that encodes a compomer.

A compomer is said to be "correlated with" a target molecule when it is known beforehand that detection of a given compomer species means that the corresponding target molecule was present in the sample being assayed. Such a correlation is due to the design of the target detection reagent, as the target detection moiety is known to specifically react with the particular target. Thus, that specific interaction allows subsequent generation of the compomer encoded by the target detection reagent. As such, a target molecule's corresponding compomer species is/are said to be "correlated with" the particular target molecule, such that detection of a particular compomer indirectly indicates the presence of the corresponding target molecule in the sample under analysis.

A "contiguous span" of molecules refers to a region within a linear polymer wherein the molecules from which the polymer was synthesized are of the same type. For instance, a contiguous span of ribonucleotides refers to a polynucleotide (or portion thereof) wherein the nucleotides within the span are all ribonucleotides. Other nucleotides, such as deoxyribonucleotides, are not included in the contiguous span, although they may be included elsewhere in the polynucleotide if the polymer comprises more nucleotides than just the contiguous span of ribonucleotides.

A "defined characteristic" refers to known characteristic that allows one compomer species to be detected and distinguished from another. Defined characteristics include defined chemical compositions, defined masses, defined lengths, defined sizes, defined sequences, and defined structures. Having a "defined chemical composition" means that the identity of each base of the compomer is known. Having a "defined molecular formula" means that the number and identity of each atom comprising the molecule is known. As a result, the mass, or mass range (due to isotopic variation) of the molecule may also be defined, i.e., the molecule has a "defined mass". For example, a specific molecular mass can be determined by summing the masses of the atoms represented in the molecule's chemical formula (e.g., $C_6H_{12}O_6$). A "mass range" reflects the range of masses that molecules having the same chemical formula may have due to the inclusion of different isotopes. Having a "defined length" or "defined size" means that it is known how many subunits comprise a particular compomer. For example, a compomer that contains ten nucleotides is said to have a length of ten nucleotides. A "defined sequence" means that the compomer has a specific sequence of nucleobases, which sequence can be determined by any suitable technique (e.g., by hybridization, sequencing, etc.). A "defined structure" means that a compomer has a three-dimensional structure (e.g., an epitope) that can be recognized by a reagent (e.g., an antibody) specifically reactive with the structure. As will be appreciated, in some cases a compomer may be classified, and thus detected by, one or more different methods, each of which is based on analysis of a particular characteristic. For example, compomers comprised of nucleobase subunits will have defined chemical compositions, masses (or mass ranges), sequences, and lengths. Accordingly, they can be detected by a variety of elemental-, mass-, sequence-, and length-based detection methods. When appropriate detection systems are employed, compomers having a unique defined characteristic (e.g., a unique defined mass, chemical composition, etc.) may readily be distinguished from other compomer species.

A "gene" refers to a particular genetic locus, or region in a DNA molecule, that encodes a gene product (i.e., polypeptide or RNA molecule). In addition to the structural coding region(s), a gene may include non-coding regions, including, introns, transcribed but untranslated regions, and regulatory elements upstream and downstream of the coding regions. Depending on the context, a "gene" may optionally comprise sequence of nucleotides required for expression of the gene (e.g., promoters, enhancers, etc.).

The term "genotype" refers to the identity of the alleles for at least some of the genes in a subject's genome. "Genotyping" a sample refers to determining the specific allele or the specific nucleotide at a particular location carried by a subject (in all or only some of its cells). Thus, a genotype may refer to one or more specific alleles.

A "hybrid" or "duplex" refers to molecule comprised of two linear polymers hybridized over at least a portion of their respective lengths to form a stable hybrid or duplex molecule. In a hybrid, each linear polymer is comprised of nucleobase subunits. Examples of such polymers include single-stranded RNA and DNA molecules comprising naturally occurring and/or modified nucleobases and/or backbone chemistries. The double-stranded regions of hybrids are sufficiently stable such that they can be maintained for the desired purpose or manipulation, for example, to serve as a primer that can be catalytically extended, such that duplexes can be separated from single-stranded molecules, if desired, etc.

"Hybridization" refers to the ability of two completely or partially complementary nucleic acid strands to come together under specified hybridization assay conditions in a parallel or preferably antiparallel orientation to form a stable structure having a double-stranded region. The two constituent strands of this double-stranded structure, sometimes called a hybrid or duplex, are held together by hydrogen bonds. Although these hydrogen bonds most commonly form between nucleotides containing the bases adenine and thymine or uracil (A and T or U) or cytosine and guanine (C and G) on single nucleic acid strands, base pairing can also form between bases which are not members of these "canonical" pairs, as is known in the art.

The term "isotopically defined" refers to a population of molecules of the same chemical formula wherein one or more of the atomic species that comprise the molecules have a more restricted isotopic distribution (due to isotopic enrichment or depletion) than occurs in nature. For example, carbon typically has several naturally occurring isotopes (e.g., $^{12}C_6$, $^{13}C_6$, and $^{14}C_6$), each of which has a different number of neutrons (6, 7, and 8, respectively). When referring to isotopes of a particular element, the formula "$^{A}X_Z$" is used, where "X" is the chemical symbol for the atom, "Z" is the atomic number (equal to the number of protons in one atom of the element), and "A" is the number of protons and neutrons combined for the particular isotope. The relative abundances for some of the naturally occurring isotopes of C, H, N, and O have been reported (see, e.g., Bievre and Taylor (1993), *Int. J. Mass. Spectrom. Ion Phys.*, vol. 123:149). For carbon, the relative abundances (expressed as a percentage) of the $^{12}C_6$ and $^{13}C_6$ isotopes are 98.90 and 1.10, respectively. For hydrogen, the relative abundances of the $^{1}H_1$ and $^{2}H_1$ isotopes are 99.985 and 0.015, respectively. The relative abundances of $^{14}N_7$ and $^{15}N_7$ isotopes of nitrogen are 99.634 and 0.366, respectively, whereas the oxygen isotopes $^{16}O_8$, $^{17}O_8$, and $^{18}O_8$ have a relative abundance of 99.762, 0.038, and 0.200, respectively. From the foregoing, a population of molecules of a particular species (e.g., a nucleoside such as adenosine) would be isotopically defined with respect to carbon if the relative abundance of the carbon atom isotopes $^{12}C_6$ and $^{13}C_6$ in the population were 99.90 and 0.10, respectively. Thus, for molecules comprised of several atomic species one or more of which has more than one naturally occurring isotope, it may be desirable to synthesize the molecule using atoms wherein the most prevalent isotope is enriched, i.e., more of it is present in relative terms as compared to the less prevalent isotope(s) of that element, or a less (or least) prevalent isotope is depleted. Methods for isotopic enrichment and depletion are known in the art.

A "label" refers to a molecule that allows a molecule attached to the label to be detected by a direct or indirect method. Here, "direct" detection refers to detection methods that do not require the interaction of another molecule with the label moiety for detection. Labels that can be directly detected include radioisotopes, luminescent molecules, fluorescent molecules, and other molecules whose presence can be detected directly. "Indirect" detection refers to methods that require one or more other molecules to interact with the label moiety in order detection to occur. Labels that can be indirectly detected include one member of a high affinity binding pair (e.g., one of biotin and streptavidin, and antigen and one or more antibodies (or antibody fragments) specific therefore, etc.)

A "library" refers to a collection of two or more different molecular species. In the context of compomers, a library comprises a plurality of different compomer species. Typically, each compomer species correlates with a different target molecule, it being understood that a "different target molecule" can mean genetic or structural variants of the same molecule (e.g., a gene or polypeptide) as well as target molecules that are different genes or polypeptides encoded by different genes. In the context of target detection reagents, a library comprises two or more different target reagent species. In any event, one member of a library differs from another due to differences in target binding moieties and/or compomer templates.

In the context of this invention, the terms "multiplex", "multiplexing", and the like refer to the ability to detect and/or analyze multiple target biomolecule species in a single assay. For example, a plurality of different target detection reagents, each specific for a different species of target biomolecule, can be used to analyze a biological sample in a single assay. If some or all of the targeted biomolecule species are present in the sample, the results of the assay will so indicate. Thus, multiplexing greatly increases assay efficiency. Typically, multiplexing allows for the analysis of more than about 10, preferably more than about 50, 100, 250, 500, or 1,000, and even more preferably more than 1,000, different species of target biomolecules in a single assay. Of course, the number of target molecule species that can be detected in a given multiplexed assay will depend on such factors as, for example, the chemical composition of the compomers encoded by the various target detection reagents employed, the type of detector used, the sensitivity of the detector, etc.

The term "mutated gene" refers to an allelic form of a gene that is capable of altering the phenotype of a subject having the mutation relative to a subject that does not have the mutated gene. If a subject must be homozygous for this mutation to have an altered phenotype, the mutation is said to be recessive. If one copy of the mutated gene is sufficient to alter the phenotype of the subject, the mutation is said to be dominant. If a subject has one copy of the mutated gene and has a phenotype that is intermediate between that of a homozygous subject and a heterozygous subject (for that gene), the mutation is said to be co-dominant. The term "mutation" as used herein refers to a difference in nucleotide sequence at a particular genetic location (e.g., nucleotide position in a gene) between or among different genomes or individuals that has a frequency below 1%.

Herein, the term "nucleic acid" refers to double- or single-stranded polymeric molecules made from naturally-occurring ribo- and deoxyribonucleotides (e.g., RNA, mRNA, rRNA, tRNA, small nuclear RNAs, DNA, cDNA, and RNA/DNA copolymers), as well as modified/non-natural nucleic acids, often known as nucleic acid mimics. Examples of nucleic acid mimics include those having phosphodiester modifications or replacements, including phosphorothioate, methylphosphonate, boranophosphate, amide, ester, and ether inter-subunit linkages, as well as complete subunit replacements with molecules such cleavage linkages (e.g., photocleavable nitrophenyl moieties) and nucleobase subunits other than nucleosides and nucleotides. A "target" nucleic acid is a nucleic acid containing a target nucleic acid sequence.

A "nucleotide sequence" refers generally to the linear sequences of nucleobases that comprise a particular nucleic acid molecule. Unless otherwise indicated, nucleotide sequences are written 5' to 3'. A "target" nucleotide sequence refers to a particular portion of the nucleotide sequence of a nucleic acid molecule present in a sample that is targeted by, and is thus substantially complementary with, the oligonucleotide portion of the corresponding target detection reagent.

"Nucleic acid amplification" refers to method for increasing the number of particular nucleic acid molecules. Nucleic acid amplification according to the present invention may be either linear or exponential, although exponential amplification is preferred.

A "nucleobase" refers to a base (i.e., a purine or a pyrimidine) capable of forming hydrogen bonds with a complementary base to form a base pair. Bases include adenine ("A"), cytosine ("C"), guanine ("G"), hypoxanthine, orotic acid, thymine ("T"), uracil ("U"), and xanthine. Base pairs include the canonical Watson-Crick DNA base pairs A:T, T:A, G:C, C:G, and in RNA, U replaces T. A "nucleobase subunit" refers to a particular monomeric subunit of a linear polymer, wherein the subunit comprises a nucleobase linked to a scaffold that permits subunit polymerization such that the resulting single-stranded polymer presents the nucleobases therein oriented such that the polymer can form a stable, double-stranded hybrid with a complementary nucleic acid molecule (e.g., a naturally occurring target nucleic acid molecule in a biological sample). Nucleosides and nucleotides represent preferred examples of nucleobase subunits useful in practicing the invention. Nucleobases may also be modified to include one or more molecules of known chemical composition in order to provide for mass modification. Such mass-modifying moieties are termed "mass tags", and the resulting mass-modified nucleobases, or nucleobase subunits, are termed "mass-tagged nucleobases" and "mass-tagged nucleobase subunits", respectively.

A "nucleoside" is a molecule that comprises a purine or pyrimidine base attached to a sugar moiety (e.g., a β-D-ribose or a β-D-2-deoxyribose) via an N-glycosidic linkage between the C-1 of the sugar and the N-9 (in the case of pyrimidine bases) or N-1 (in the case of purine bases). The sugar moiety is 2'-deoxyribose in the case of a deoxyribonucleotides and a ribose moiety in the case of a ribonucleotide. Analogs of deoxyribose and ribose can also be used, including 2',3'-deoxy as well as a vast array of other nucleotide mimics that are well-known in the art. Mimics include chain-terminating nucleotides, such as 3'-O-methyl, halogenated base or sugar substitutions; alternative sugar structures including non-sugar, alkyl ring structures. Representative examples of nucleosides include adenosine, cytidine, guanosine, inosine, orotidine, thymidine, uridine, and xanthosine. A "nucleoside subunit" refers to a particular nucleoside of a polynucleotide.

A "nucleotide" refers to a nucleoside having one or more phosphate groups esterified to the 5'-carbon atom of its sugar moiety. Nucleotides may either be naturally occurring or synthetic. Representative examples of nucleotides useful in the practice of the invention include adenosine mono-, di-, and tri-phosphate; cytidine mono-, di-, and tri-phosphate; guanosine mono-, di-, and tri-phosphate; inosine; orotidine; thymidine mono- and tri-phosphate; uridine mono-, di-, and tri-phosphate; and xanthosine.

An "oligonucleotide" is a polymer made up of two or more nucleoside and/or nucleobase subunits coupled together, for example, by the polymerization of nucleotides. An oligonucleotide may be comprised of nucleobase subunits that include, for example, nucleobases found in DNA and/or RNA and analogs thereof. When the nucleobase subunits are nucleosides, the sugar groups of the nucleoside subunits may be ribose, deoxyribose, or analogs thereof, including, for example, ribonucleosides having a 2'-O-methyl substitution to the ribofuranosyl moiety. The nucleobase subunits may by joined by linkages such as phosphodiester linkages, modified linkages, or by linkages between non-nucleotide moieties which do not prevent hybridization of the oligonucleotide to its complementary target nucleic acid sequence. Modified linkages include those linkages in which a standard phosphodiester linkage is replaced with a different linkage, such as a phosphorothioate linkage or a methylphosphonate linkage. The nucleobase subunits may be joined, for example, by replacing the natural deoxyribose phosphate backbone of DNA with a pseudo-peptide backbone, such as a 2-aminoethylglycine backbone that couples the nucleobase subunits by means of a carboxymethyl linker to the central secondary amine. DNA analogs having a pseudo-peptide backbone are commonly referred to as "peptide nucleic acids" or "PNAs" (see, e.g., U.S. Pat. No. 5,539,082. Other non-limiting examples of oligonucleotides or oligomers contemplated by the present invention include nucleic acid analogs containing bicyclic and tricyclic nucleoside and nucleotide analogs referred to as "locked nucleic acids," "locked nucleoside analogues," or "LNAs" (see, e.g., U.S. Pat. No. 6,083,482). Any nucleic acid analog is contemplated by the present invention, provided that the modified oligonucleotide can hybridize to a target nucleic acid under stringent hybridization assay conditions or amplification conditions. Oligonucleotides having a defined sequence of nucleobase subunits may be produced by techniques known to those of ordinary skill in the art, such as by chemical synthesis or other suitable methods.

An oligonucleotide is "substantially complementary" to its corresponding target nuclei acid molecule when it contains at least 6, and preferably at least 8, 9, 10, 11, 12, 13, 14, 15, or more contiguous nucleobases that are at least 80% complementary, preferably at least 90% complementary, and most preferably 100% complementary, to a contiguous span of nucleotides in the corresponding target nucleic acid. Those skilled in the art will readily appreciate modifications that could be made to the hybridization assay conditions at various percentages of complementarity to permit hybridization of the oligonucleotide to the target sequence while preventing unacceptable levels of non-specific hybridization. The degree of complementarity is determined by comparing the order of nucleobases making up the two regions over which complementarity is being compared, and does not take into consideration other structural differences which may exist between the two nucleic acids, provided the structural differences do not prevent hydrogen bonding between complementary bases. The degree of complementarity between two nucleic acids can also be expressed in terms of the number of nucleobase mismatches present in the regions being compared, which may range from 0 to 4, preferably 0 to 2, nucleobase mismatches.

A "patentable" composition, process, machine, or article of manufacture according to the invention means that the subject matter satisfies all statutory requirements for patentability at the time the analysis is performed. For example, with regard to novelty, non-obviousness, or the like, if later investigation reveals that one or more claims encompass one or more embodiments that would negate novelty, non-obviousness, etc., the claim(s), being limited by definition to "patentable" embodiments, specifically excludes the unpatentable embodiment(s). Also, the claims appended hereto are to be interpreted both to provide the broadest reasonable scope, as well as to preserve their validity. Furthermore, if one or more of the statutory requirements for patentability are amended or if the standards change for assessing whether a particular statutory requirement for patentability is satisfied from the time this application is filed or issues as a patent to a time the validity of one or more of the appended claims is again analyzed, the claims are to be interpreted in a way that (1) preserves their validity and (2) provides the broadest reasonable interpretation under the circumstances.

A "plurality" means more than one.

The term "polymorphism" refers to the occurrence of two or more alternative genomic sequences or alleles between or among different genomes or individuals. Thus, "polymorphic" refers to the coexistence of more than one form of a gene or portion (e.g., allelic variant) thereof. A portion of a gene of which there are at least two different forms, i.e., two different nucleotide sequences, is referred to as a "polymorphic region" of a gene. A polymorphic region can comprise as little as a single nucleotide, the identity of which differs in different alleles. A "single nucleotide polymorphism" or "SNP" is a single base pair change. Typically, a single nucleotide polymorphism occurs as the result of a replacement of one nucleotide by another nucleotide at the polymorphic site. Deletion or insertion of a single nucleotide can also give rise to single nucleotide polymorphisms. A polymorphic region can also involve multiple contiguous nucleotides, as in substitutions, rearrangements, insertions, and deletions of several nucleotides, although these polymorphisms are less common A "polynucleotide" refers generally to a linear polymer of nucleotides, although if the polymer contains one or more nucleobase subunits other than a nucleotide or nucleoside, for purposes of the invention it shall still be considered a polynucleotide. Preferred polynucleotides are those in which the various subunits are linked by internucleotide 5'-3' phosphodiester linkages. Polynucleotides include single- and double-stranded DNA and RNA molecules, including those where one or both strands are generated recombinantly or synthetically.

A "polypeptide" refers to a molecule comprising a polymer of amino acid residues (which include native and non-native amino acid residues). Thus, polypeptides include peptides and proteins, including native and engineered proteins, enzymes, antibodies, antibody fragments, and protein conjugates. In preferred embodiments, polypeptides are antibodies, antibody fragments, enzymes, receptors, receptor ligands, regulatory proteins, nucleic acid-binding proteins, hormones, or protein product of a display method, such as a phage display method or a bacterial display method.

The term "preferentially hybridize" means that under stringent hybridization assay conditions, complementary nucleic acids (or complementary portions of nucleic acids that also contain non-complementary portions) hybridize to form stable hybrids. Preferential hybridization can be measured using standard techniques. Preferably, there is at least a about 10-fold difference in hybridization between one nucleic acid species and its complementary nucleic acid, as compared with a non-complementary nucleic acid, more preferably at least about a 100-fold difference, and most preferably at least about a 1,000-fold difference. Preferably, the reaction conditions are such that hybridization between non-complementary nucleic acids in a test sample is no more than the background signal level.

A "probe" refers to a molecule that minimally comprises at least one target binding moiety. Probes may thus comprise two or more target binding moieties that may be linked to form the probe. For example, a particular probe may comprise two oligonucleotides which, when hybridized to their respective target molecules, become juxtaposed such that they can be linked (e.g., ligated) to form a complete probe molecule. Probes (or their constituent parts) may also contain other components, including labels and tags. Tags serve as moieties that allow the molecules to which they are attached to be isolated from other molecules present in a mixture (e.g., a solution).

A "promoter" means the minimal DNA sequence sufficient to direct transcription of a polypeptide encoded by a DNA molecule to which the promoter is operably linked, i.e., there is a functional linkage between the promoter and the coding sequence (e.g., a compomer-encoding region) such that the coding sequence can be transcribed by an RNA polymerase. In general a "promoter" refers to a variety of nucleic acid control sequences that can direct transcription of a nucleic acid. As used herein, a promoter includes the necessary nucleic acid sequences for RNA polymerase binding, transcription initiation, and elongation. Promoters can be either prokaryotic or eukaryotic in origin, with bacteriophage promoters such as the T7, T3, and SP6 promoters being preferred. Eukaryotic promoters include, among others, promoters from CMV, SV40, retroviruses, and adenoviruses. A promoter also optionally includes distal enhancer or repressor elements that can be located as much as several thousand base pairs from the start site of transcription. Promoters also include "consensus" promoters, which do not naturally but can be designed, for example, by comparing the promoter sequences of genes transcribed at high levels to develop a promoter sequence that reflects a "consensus" base (typically the nucleotide most frequently represented at the particular nucleotide position among the sequences being compared) at least one, preferably some, and most preferably all, of the nucleobase subunits comprising the promoter.

The term "reacting conditions" means reaction conditions that permit molecules that specifically interact with each other to preferentially interact. Reacting conditions include temperature, solute concentrations, pH, ionic conditions, etc. Stringent hybridization conditions are representative reacting conditions in the context of nucleic acid hybridization.

The term "reactive group" refers to a chemical moiety of a larger molecule that is capable of a reacting with a reactive group of another molecule using a specific chemistry.

The terms "separated", "purified", "isolated", and the like mean that one or more components of a sample contained in a sample-holding vessel are or have been physically removed from, or diluted in the presence of, one or more other sample components present in the vessel. Sample components that may be removed or diluted during a separating or purifying step include, proteins, carbohydrates, lipids, inhibitors, non-target nucleic acids, and unbound probe molecules. With target capture procedures, target nucleic acids bound to immobilized capture probes are preferably retained in the sample during the separating or purifying step.

The term "species" is used herein in various contexts, e.g., compomer species, target molecule species, nucleotide species, etc. In each context, the term refers to a population of chemically indistinct molecules of the sort referred in the particular context. For example, a "compomer species" is a population of compomers having the same chemical composition, and thus effectively the same mass. Of course, due to the occurrence of isotopic variation in molecules having an identical chemical structure, molecules within a given species may have slightly different masses, and thus the "mass" for a given molecular species (e.g., a compomer) in fact represents a small mass range. Depending on factors such as the level of multiplexing in a given assay, the sensitivity of the analytical system being used, etc. it may be desired to synthesize compomers from isotopically defined subunits (e.g., ribonucleotide triphosphates) to more tightly define the small mass range of a particular compomer and thereby enhance the resolution of mass peaks that appear in spectra resulting from analysis of the sample.

Herein, "stable" refers to an interaction between two molecules (e.g., the strands of a nucleic acid duplex over their regions of complementarity) that is sufficiently stable such that the molecules can be maintained for the desired purpose or manipulation. For example, a "stable" interaction between a primer and its cognate primer binding site refers to one that will allow the primer to be extended under reaction conditions suited for primer extension reactions.

The phrases "stringent hybridization assay conditions," "hybridization assay conditions," "stringent hybridization conditions," "stringent conditions", and the like mean reaction conditions that permit complementary nucleic acids (e.g., an oligonucleotide, or a target sequence binding region of an oligonucleotide that further comprises other regions, and a nucleic acid having a base sequence complementary thereto) to preferentially hybridize. Stringent hybridization assay conditions may vary depending upon various factors, including the GC content and length of the regions of complementarity between the nucleic acids, the degree of similarity between the complementary sequences and other sequences that may be present in the sample. Hybridization conditions include the temperature and the composition of the hybridization reagents or solutions.

A "subunit" refers to a portion of a larger molecule. Thus, a polymer is comprised of two or more subunits. Exemplary subunits include individual amino acids, nucleobase subunits, nucleosides in a DNA or RNA and individual nucleotides used to synthesize a nucleic acid or oligonucleotide, as well as subunit multimers (e.g., molecules that comprise two, three, four, or more subunits, e.g., nucleotides) that can be used, for example, as intermediates in oligonucleotide or peptide synthesis. In other contexts, if an oligonucleotide contains two distinct regions, e.g., a target binding moiety and a compomer template, each of the distinct regions may be referred to as a subunit of the oligonucleotide.

A "tag" is a moiety that can be attached to or included as part of another molecule to facilitate separation of tagged molecules from non-tagged molecules in an assay. Representative examples of molecules that may be tagged include target detection reagents, cleavage substrates, and compomers.

A "target binding moiety" refers to a molecule capable of specific molecular recognition. Molecules capable of specific molecular recognition are capable of specific binding interactions with other molecules. In particular, a target binding moiety is the portion of a target detection reagent according to the invention that is capable of specifically interacting with and binding to a target molecule. Preferred target binding moieties are comprised of polynucleotides (e.g., oligonucleotides) and polypeptides (e.g., antibodies and antibody fragments), as well as aptamers (i.e., synthetic nucleic acid molecules that specifically bind to or otherwise interact with other molecules, including proteins and small molecules), and small molecules (i.e., naturally occurring or synthetic organic molecules having a molecular mass of less than about 10,000 Da that specifically bind to or otherwise interact with a biomolecule species of interest, for example, a target protein).

The term "target molecule" or "target" refers to a molecule the presence, absence, or abundance of which is to be determined. Preferred targets are biomolecules, including polypeptides and nucleic acid molecules.

A "target nucleic acid" refers to a nucleic acid molecule containing a target nucleic acid sequence, which sequence is typically comprised of nucleotides. Target nucleic acids can be single or double-stranded. In double-stranded molecules, the strands are preferably separated over at least that portion including the target nucleotide sequence in order to facilitate hybridization of target binding moiety of a target detection reagent specific for the particular target nucleotide sequence.

By "target nucleic acid sequence," "target nucleotide sequence," "target sequence," or "target region" is meant a specific deoxyribonucleotide or ribonucleotide sequence comprising all or part of the nucleotide sequence of a target nucleic acid molecule.

A "target sequence binding region" refers to a nucleic acid molecule, e.g., an oligonucleotide, that has a base sequence sufficiently complementary to its target nucleic acid sequence to form, for example, an oligonucleotide:target hybrid stable for detection under stringent hybridization assay conditions. Typically, a target sequence binding region comprises at least about 6 nucleobase subunits, preferably between 6 to about 500 or 1,000 nucleobase subunits.

A "transcription unit" refers to a molecule that encodes a compomer or a cleavage substrate according to the invention. A transcription unit serves at the template for synthesizing a compomer according to the invention. Synthesis of compomers preferably occurs by transcription of the compomer-encoding region of the transcription unit. Thus, transcription units preferably at least include a functional promoter and a compomer-encoding region.

In the context of this invention, "unique" refers to a molecular species that differs in one or more distinguishable ways from the other molecular species present. Preferably, in the context of compomers, each compomer species generated in a particular reaction will be unique as compared to each of the other compomer species produced in the reaction. Thus, even if all of the compomer species present in a given reaction are to be analyzed, for example, based on a single defined characteristic (e.g., mass), the mass (or mass range) of each compomer species will be sufficiently different from the other compomer species present such that it can be detected and resolved in the context of the particular assay. In the context of target molecules, a "unique target molecule" refers to a target molecule species that can be distinguished from each of the other target molecule species in a given reaction. As will be appreciated, a single gene (or other genetic locus comprising a contiguous span of nucleotides (preferably from about 10 to about 1 million or more nucleotides) may contain multiple sites that can be independently targeted by different target detection reagent species (which species differ from one another due to different target detection moieties, and preferably due also to different compomer template species that encode distinguishable compomer species).

SUMMARY OF THE INVENTION

The present invention provides reagents and methods for the efficient analysis of a sample to determine whether it contains one or more different species of target molecules. In accordance with the invention, detection of one or more particular target molecule species in a sample occurs indirectly, in that the detection step does not involve direct detection of the target molecule(s). Instead, a particular target is detected by detecting a compomer correlated therewith. In this invention, indirect detection of a particular species of target molecule is accomplished by generating the corresponding compomer species during an assay. Thus, a compomer species will be available for detection only if the target molecule with which it is correlated is present in the sample.

Each compomer species is engineered to comprise polymerized subunits arranged to produce a molecule having a defined characteristic, e.g., one or more of a defined chemical composition, a defined molecular formula, or a defined mass, sequence, length, or structure, that enables it to be detected in a complex mixture such that detection of the compomer indicates that the target molecule is present in a sample. In order to allow a compomer correlated with a target molecule to be generated during the course of an assay, a compomer template (or a complement thereof) encoding the desired compomer is provided as part of a target detection reagent specific for the particular species of target molecule. Target specificity is imparted to target detection reagents by way of including one or more target binding moieties linked to the compomer template. Thus, whether a target molecule exists in a sample can be determined by contacting the sample with a target detection reagent specific for the target molecule to form reagent: target complexes. In some embodiments, it may be helpful to remove target detection molecules that have not interacted with their cognate target molecules (e.g., because the targets are not present in the sample, the target molecules are present but at a concentration that results in saturated binding due to excess target detection reagent molecules, etc.) prior to generating compomers. In other embodiments, a complete target detection reagent specific for a particular target may be formed only in the presence of a particular target molecule species, thereby limiting any advantage that may be obtained by an intermediate purification, isolation, or separation step.

If a target molecule is present in the sample, the target binding moiety of the target detection reagent will bind to it. Thereafter, the compomer template, which comprises a compomer-encoding region, is used to guide generation of the encoded compomer (or a larger precursor that includes the compomer). As a given compomer is correlated with, and thus indicative of the presence in a sample of a particular target molecule, detection of the compomer indirectly indicates that the corresponding target molecule is present in the sample. Further, because a particular compomer species has a defined characteristic that allows it to be distinguished from other compomer species that may have also been generated in an assay, a plurality of different compomer species can be detected in a single assay, thereby allowing multiplex analysis of complex samples, e.g., biological samples, for many different target molecule species, particularly target biomolecules (e.g., nucleic acid molecules, polypeptides, lipids, and carbohydrates).

Thus, one aspect of the invention relates to patentable target detection reagents that each comprise a target binding moiety and a compomer template, or complement thereof, encoding a compomer, the detection of which indirectly indicates the presence of a particular target molecule correlated with the particular compomer. In general, a target binding moiety comprises a molecule specific for a target molecule, such that the target detection reagent can specifically bind to or otherwise react with the target molecule in an assay. In some embodiments, the target binding moiety comprises a polypeptide, preferably an antibody, an antibody fragment, a receptor, or a ligand for a receptor that is specific for the target molecule. In other embodiments, the target binding moiety comprises a nucleic acid molecule (e.g., an oligonucleotide) that specifically targets a target nucleotide sequence in a target nucleic acid molecule. In still other embodiments, the target binding moiety comprises an aptamer or a small molecule.

Regardless of the target binding moiety(ies) included in a target detection reagent of the invention, the target detection reagent also includes at least one compomer template, or complement thereof, linked directly or indirectly (i.e., through a linker) to the target binding moiety. As will be appreciated, a compomer template minimally encodes a compomer, the detection of which indirectly indicates the presence of a particular target molecule species in a sample being studied. In some embodiments, a compomer template encodes a cleavage substrate, which is an molecule that comprises a compomer and at least one additional subunit that can be released from the cleavage substrate to yield a compomer. In preferred embodiments, compomer templates are nucleic acid molecules, particularly oligonucleotides.

Compomers can be generated from compomer templates by any suitable process that allows subunits to be polymerized using the compomer template to guide compomer (or cleavage substrate) generation. In preferred embodiments, a compomer template (or complement thereof) encodes a transcription unit. Functional transcription units comprise a promoter region operatively linked to a compomer-encoding region. Transcription from the transcription unit results in the production of a compomer, or, if the compomer-encoding region codes for additional nucleotides, a cleavage substrate from which the compomer can be subsequently released. In other embodiments, compomers (or cleavage substrates) are produced from the compomer template by another process, for example, by an extension reaction (e.g., primer extension), which may or may not be catalyzed enzymatically.

Thus, another aspect of the invention concerns a patentable class of molecules termed compomers useful in a variety of chemical analyses. Specifically, detection of a compomer indirectly indicates that the target molecule (including biomolecular targets) correlated therewith is present in a sample. Unlike previously reported mass tags and the like, compomers are synthesized during the course of a particular chemical analysis following reaction with or binding of the target detection moiety of the target detection reagent to the target molecule. Thereafter, compomers are synthesized and detected based on their defined characteristic(s), e.g., chemical composition, molecular formula, mass (e.g., by mass spectrometry), length (e.g., by electrophoretic mobility), size (e.g., by chromatography), subunit sequence (e.g., by hybridization to an oligonucleotide probe), etc. using a suitable detection system. The defined characteristic(s) of a compomer species allows it to be distinguished from other compomer species. Of course, because the sequence and identity of subunits used to synthesize a compomer may be independent of the target molecule correlated therewith, subunits can be selected using other criteria, for example, ease of polymerization, cost, stability, detection format, etc. For this reason, compomer species can be engineered to optimize differences between species, which can be helpful to resolve multiple compomer species that, for example, may be generated simultaneously during a particular multiplex assay.

As will be appreciated, assays that employ compomers to signal the presence of particular target molecules in a sample greatly simplify the biochemical procedures required to analyze a sample. Moreover, because the defined characteristic(s) of compomers can be engineered for use with specific detection systems, a plurality of different compomer species can be generated and resolved in a single assay, facilitating multiplex analysis of complex samples such as biological samples.

Compomers (and cleavage substrates) are synthesized from subunits using a compomer template portion of a target detection reagent as a guide. If desired, monomeric subunits for compomer generation can be assembled into dimers, trimers, and other intermediate subunit polymers prior to their inclusion in any assay. In any event, a compomer template guides the serial addition of subunit species to the growing molecule. In preferred embodiments, compomer templates comprise polymers of nucleobase subunits having a defined nucleobase sequence of –. Hence, a compomer generated from such a template molecule will have a corresponding sequence of subunits (e.g., nucleobases) ordered in accordance with the compomer template molecule. Nucleosides and nucleotides represent particularly preferred subunit classes for the synthesis of compomers comprised of subunits containing nucleobases. Indeed, when compomers are synthesized from nucleotide triphosphates (i.e., nucleotides having three phosphate groups attached via esters to the C-5' position of the sugar moiety), it is preferred to use appropriate enzymes to catalyze their synthesis. Particularly preferred enzymes useful for this purpose are DNA-dependent RNA polymerases, such as the T7, T3, and SP6 RNA polymerases, in which event the nucleotides are preferably ribonucleotides. For compomers generated from a primer by way of primer extension, for example, preferred enzymes include the DNA polymerases Taq, Klenow fragment, T4, T7, and $E.\ coli$ DNA polymerase I, and retroviral reverse transcriptases.

In other embodiments, compomers may be comprised of amino acid or saccharide subunits. In embodiments employing amino acids, their sequence is typically dictated by an RNA molecule transcribed from a compomer template (or a nucleic acid product derived therefrom). Thus, in these embodiments, the RNA transcribed (or otherwise generated) from the compomer template serves as an intermediate (i.e., a "compomer intermediate") for subsequent generation of the compomer. For example, following transcription, the mRNA can be translated to generate peptide-based compomers, or larger precursors from which compomers can be subsequently released (e.g., by suitable physical, chemical, or enzymatic techniques) and detected using an appropriate detection system. In embodiments where the compomer intermediates are peptides translated from an mRNA transcribed from a compomer template, the peptides are preferably synthesized from mRNA templates in an in vitro translation reaction.

In still other embodiments, compomers are synthesized from compomer templates non-enzymatically. For example, nucleobase subunits designed for polymerization by a suitable polymerization chemistry can be used. In such embodiments, compomers are typically synthesized by the serial elongation of a nascent compomer polymer, whereby in each step, a new subunit is polymerized to a reactive group on a terminal residue of the growing polymer. Such syntheses generally occur through multiple rounds of deprotection and coupling to ensure incorporation of all of the subunits in the largest possible compomers encoded by the target detection reagents used in the assay.

Depending on the compomer template included in a particular target detection reagent, some compomers may initially be generated as part of larger precursors that require further processing before compomer detection. Thus, another aspect of the invention concerns such precursors. Such precursors, termed "cleavage substrates", comprise at least two different monomeric subunit species and contain at least two regions, a compomer and another region that can be separated from the compomer prior to detection. When cleavage substrates are employed, the compomer portion preferably lacks at least one of monomeric subunit species found in the larger precursor molecule. Alternatively, a cleavage substrate, or plurality of cleavage substrates, may include an element such as an endopeptidase cleavage site. Whatever the case, the terminal portion of the cleavage substrate is preferably cleaved to release the compomer, the presence of which can then be detected. A compomer can be released from a cleavage substrate, for example, by chemical, physical, or enzymatic cleavage. Preferably, the cleavage is subunit-specific and is targeted to one or more of the subunit species absent in the compomer portion of the cleavage substrate. The separation of a compomer from a larger precursor ensures that the compomers generated in a particular assay will exhibit the defined characteristic that enables their subsequent detection and correlation with the corresponding target molecule. The region cleaved from a cleavage substrate to yield a compomer contains at least a portion of a monomeric subunit. When the cleaved region comprises more than one monomeric subunit, the subunits may, for example, be of the same or different species, with at least one them being of a species different from the monomeric subunit species present in the compomer. In other embodiments, the cleaved region may contain one or more subunits of the same species as comprises the compomer. In other embodiments, the compomer is not generated as part of a larger precursor. Instead, synthesis from the compomer template (or compomer intermediate) results directly in the particular compomer, free from any portions that must be removed prior to detection.

Compomers typically comprise from one to about 1000 monomeric subunits (e.g., individual nucleobase subunits (particularly ribonucleotides), amino acids, etc.), although larger subunits comprised of several monomeric subunits can also be used, particularly when non-enzymatic polymerization chemistries are employed. Particularly preferred are compomers that comprise from about 3 to about 10, 20, 50 and 100 monomeric subunits. In many embodiments, particularly those wherein the various compomer species will be released from corresponding cleavage substrates prior to detection, it is preferred that the compomer regions be engineered to comprise fewer than all of the subunit species that might be used in a given reaction. For example, when a cleavage substrate is synthesized enzymatically from ribonucleotides, it is preferred that the compomer portion comprise only one, two, or three subunit (here, ribonucleotide) species, with the other portion(s) of the cleavage substrate containing one or more subunits at least one of which is not present in the compomer and which can thus be used to release the compomer from the cleavage substrate. Of course, in some embodiments that employ a cleavage substrate, it is not necessary for the compomer to contain fewer subunit species than contained in the precursor, as techniques that rely on the presence of two or more specific subunits to effect release may also be employed. For instance, a peptide-based cleavage substrate can be engineered to include an amino acid sequence that is specifically cleaved by a protease. In such embodiments, the proteolytic cleavage separates the compomer from the remainder of the cleavage substrate.

As individual compomer species are engineered to have at least one defined characteristic (e.g., a specific chemical compositions, molecular formula, mass (or mass range), length, size, structure, etc.) that allows one compomer species to be distinguished from all other compomer species that may be generated in an assay, it is preferred that the defined characteristic(s) of a particular compomer species be narrowly defined. For example, in embodiments where the defined characteristic is mass, narrow definition of mass means that the mass, and more likely the mass range for the species (due to isotopic variation among the atoms making up the molecules of the particular compomer species), is narrow. To minimize the mass range for a compomer species, as is particularly preferred in highly multiplexed assays that employ mass-based detection systems (e.g., mass spectrometers), the compomer (or cleavage substrates) can be generated using subunits that are isotopically defined. Of course, because isotopically defined subunits may be more costly to procure that comparable reagents comprised of atoms that have not been enriched or depleted for a particular isotope, in such embodiments it is preferred that cleavage substrates include as few subunits as possible (preferably no more than about 100, preferably less than about 25, and preferably 10, 9, 8, 7, 6, 5, 4, 3, 2, or 1) outside of the compomer regions.

Because compomers are engineered in terms of subunit sequence and/or composition to provide one or more defined characteristics (e.g., a defined mass, chemical composition, molecular formula, or mass range, length, sequence, and/or structure), many different compomer species can be generated in a given assay, if desired. The maximum number of compomer species that can be used in a given assay will depend on many factors, including the subunit composition of the compomers, whether some or all of the compomers are isotopically defined (in embodiments wherein mass is the defined characteristic), the detection system employed, the range of, for example, masses that can accurately be detected by the detection system employed (in embodiments wherein mass is the defined characteristic), the sensitivity of the detector used, the software used to analyze the resulting data, the number of target molecule species being assayed for, etc.

In certain preferred embodiments, mass is the defined characteristic used to distinguish compomer species. As a result, in such embodiments compomers are typically detected using mass-based detection techniques, with mass spectrometry being preferred. While it is envisioned that any known mass spectrometry method can be used to detect compomers, preferred methods are direct laser-desorption ionization mass spectrometry (with no matrix), electrospray ionization mass spectrometry, secondary neutral mass spectrometry, and secondary ion mass spectrometry are preferred. A particularly preferred method is matrix-assisted laser-desorption ionization mass spectrometry. In other preferred embodiments, the defined characteristic is compomer length. As a result, compomer species can be distinguished by size separation techniques, preferred examples of which include electrophoresis and chromatography. In other embodiments, the defined characteristic is chemical composition.

As will be appreciated, a plurality of different compomer species can be designed and then encoded in compomer template libraries on such factors as the detection system to be used in a given assay, the number of target molecule species that might be detected in a given assay (and thus the level of multiplexing), whether isotopically defined subunits are available to synthesize compomers (in the context of assays that employ mass detection to detect compomers), etc., the number of compomer templates in a given library may differ. Preferably, in a given library the different compomer template species will be designed to guide the generation of compomer species that can be readily resolved by the particular detection system to be employed. In many embodiments, the compomer templates will encode cleavage substrates. Because the sequence of subunits that comprise a given compomer is independent of target identity, the same set of compomers may be used to detect different sets of target molecules, as the target binding moiety of a given target detection reagent determines target specificity. Thus, different target detection reagent libraries can be assembled using a single compomer template library, or a portion thereof, linked to different libraries of target binding moieties. As will be appreciated, for a particular target detection reagent library, the components of each target detection reagent species are known, thereby allowing compomer species to be correlated with targets, such that detection of a compomer encoded by a particular target detection reagent indirectly signals the presence in the sample of the target recognized by the target detection reagent. Compomer templates, alone or assembled into target detection reagents, can be packaged and sold as kits. Such kits may include multiple compomer template or target detection reagent species. When a plurality of different species are packaged, in some embodiments they may be individually packaged, whereas in other, some or all of them may be packaged separately. Moreover, compomer templates and target detection reagents are preferably prepared as isolated, purified reagents, and they may be stored in liquid or solid form.

Another aspect of the invention relates to methods of making compomers using the compomer templates of the invention. In such methods, after a target binding moiety of a target detection reagent binds to its corresponding target molecule to form a reagent:target complex, the compomer template is used to generate the compomer (or cleavage substrate) encoded by the compomer-encoding region thereof. In some embodiments, the target detection reagent may further include one or more tag moieties, which moieties may be used to purify, isolate, or separate reagent:target complexes (and unreacted target detection reagent molecules) from other components in an assay, including target detection reagents that have not reacted with target molecules.

In embodiments where the target detection reagent includes a complement of a compomer template, the compomer template is produced prior to compomer generation. In some preferred embodiments, the compomer template comprises a transcription unit, and the compomer encoded thereby is generated by transcribing the compomer-encoding region using an RNA polymerase (preferably a DNA-dependent RNA polymerase) that can direct transcription of nucleic acids functionally associated with the particular promoter included in the transcription unit. In other embodiments that do not involve transcription, for example primer extension or subunit polymerization using the compomer template as a guide, suitable reaction conditions are provided to allow for compomer (or cleavage substrate) generation. In embodiments where compomer template encodes a cleavage substrate, following generation of the cleavage substrate the compomer is preferably separated from the additional subunits included in the cleavage substrate that do not constitute a part of the compomer.

As those in the art will readily appreciate, this invention provides for increased accuracy, efficiency, and reliability of methods designed to indirectly detect the presence of one or more species of target molecule in a sample, particularly in complex samples such as biological samples obtained from patients, for example, for purposes of diagnostic or prognostic screening. Preferably, assays performed in accordance with the invention employ one or more controls to reduce the risk of false negative or positive results. The methods of the instant invention can also be performed quickly (e.g., in few as about 2-3 hours) and cost-effectively, as specialized reagents (other than target detection reagents according to the invention) are not required. As such, they will find widespread application in the biological sciences. Thus, other aspects of the invention concern applications for the methods of the invention. As will be appreciated, the methods can be used for many purposes, including to diagnose (e.g., pre-natally or post-natally) a genetic disease, a genetic predisposition to a disease or condition (e.g., obesity, atherosclerosis, or cancer), infection by a pathogen (e.g., a virus, bacteria, parasite, or fungus), or to provide information relating to identity, heredity (e.g., paternity), compatibility (e.g., HLA phenotyping for purposes of tissue transplantation), or responsiveness to a proposed drug or therapeutic regimen.

The summary of the invention described above is non-limiting and other features and advantages of the invention will be apparent from the following figures, detailed description of the invention, and from the claims.

BRIEF DESCRIPTION OF THE FIGURES

The following drawings form part of the present specification and are included to further demonstrate certain aspects and embodiments of the present invention. The invention may be better understood by reference to one or more of these drawings in combination with the detailed description of specific embodiments presented herein.

FIG. 1 diagrammatically illustrates the general structure of a target detection reagent according to the invention. As shown, a target detection reagent comprises a compomer template (CT) linked to a target binding moiety (TBM). The CT-TBM linkage (X) may be directly between reactive groups on the respective compomer template and target binding moiety portions or by way of a linker molecule (or group of molecules) disposed between the compomer template and target binding moiety. Preferably, linkages between the various components are covalent.

FIG. 2 diagrammatically illustrates the general structure of a compomer template of a target detection reagent of the invention. In this representative illustration, the compomer template comprises a compomer-encoding region and a terminator, although it is understood that a terminator region is an optional element. When included, the terminator allows for strict definition of the ultimate terminus of the encoded compomer. Examples of terminator regions include those comprising chain-terminating subunits (such that additional subunits can not be added to the nascent compomer, cleavage substrate, or other intermediate beyond the chain-terminating subunit, e.g., a dideoxynucleotide), cleavage bases, etc. Preferably, each member of a compomer template library that includes terminator regions will encode the same terminator, thereby, for example, facilitating removal of the terminator regions by, for example, cleavage of a cleavage base. Compomer templates are comprised of subunits that can be polymerized using suitable chemistry, including enzymatic processes. The subunits of the compomer template serve a template for generating a compomer having defined characteristics.

FIG. 3 diagrammatically illustrates certain preferred embodiments compomer templates according to the invention. In these embodiment, the compomer template may optionally include a terminator, as well as a region before the compomer-encoding region, which in the figure is designated "Y". When included, the Y region also includes one or more subunits, for example, nucleobase subunits. These additional subunits, if a Y region is present, are preferably of the same class as the subunits of the compomer-encoding region (e.g., nucleobase subunits when the compomer-encoding region comprises nucleobase subunits). As will be appreciated, differences between the compomer definition regions in various compomer templates distinguishes one species from another, and ultimately allows the different compomer species encoded thereby to be distinguished from one another.

FIG. 4 diagrammatically represents a preferred class of compomer templates according to the invention that build on those illustrated in FIG. 3. Here, an additional element, a promoter- or primer binding site-encoding region (or a regions that includes both a primer binding site and a promoter) is depicted. In those embodiments where the compomer template codes for a promoter, if necessary the template also codes for additional sequences ultimately required for transcription initiation (here, designated as the "Y" region).

FIG. 5 illustrates preferred embodiments of formulas for compomer templates according to the invention that are similar to those shown in FIG. 3, the difference being that in this figure the compomer definition region is defined to comprise 1-5 examples of a nucleobase subunit sequence defined by the formula $A_xC_yG_z$, where x ranges from 0-5 and y and z each independently range between 0 and 10.

FIG. 6 illustrates a representative example illustrating the assembly of a plurality of different target detection reagent species from members of already-existing component libraries. As depicted in this figure, the single compomer template library contains compomer template species 1, 2, 3, through n (CT1, CT2. CT3, through CTn), target binding moiety library 1 contains x species of target binding moieties (numbered TBM1-1, TBM1-2, TBM1-3, through TBM1-x), each of which targets a different target nucleic acid (e.g., different genetic variations), and target binding moiety library 2 contains y species of target binding moieties (numbered TBM2-1, TBM2-2, TBM2-3, through TBM1-y), each of which targets a different polypeptide species, e.g., a disease-associated protein. Which target binding moieties to include in the five target detection reagent species shown depends on the target molecules to be detected in the particular assay. Here, four of the target molecule species are nucleic acids, while the fifth species is a polypeptide. After the deciding which of target binding moieties are to be used (based on the specific targets to be assayed), a decision is made on which compomer templates to use, and whether a linker (L) will be used to attached given compomer template to the target binding moiety it has been assigned. The five target detection reagents (TDR1-5) are then assembled. As the defined characteristics of individual compomer species do not depend on the identity of a particular target, compomer templates may be assembled with target binding moieties without regard for target sequence, structure, or the like. However, the assembly of a particular compomer template and a particular target binding moiety into a target detection reagent results in the compomer becoming correlated with the particular target, and vice versa.

FIG. 7 schematically illustrates several particularly preferred embodiments of compomer templates according to the invention. In each of these embodiments, the compomer template encodes a promoter (a T7 promoter in three of the compomer templates and an SP6 promoter in the other three of the compomer templates), a transcription start codon, a compomer specificity region (i.e., the regions in the various compomer species engineered to allow the compomer species to be distinguished during the detection stage of the particular analysis), and a cleavage base. Such compomer templates, and the compomers they encode, provide for extremely high levels of multiplexing, particularly when coupled with MALDI detection systems. In the embodiments illustrated in this figure, each compomer comprises from one to three different nucleotide subunit species, with the cleavage base comprising a nucleotide subunit not represented in the compomer region. In each compomer, k, x, y, and z are independently selected integers that range from 0 to 1,000 or more, typically 0-100, preferably 0-50, with the understanding that within a given library, the compomer specificity region of each compomer template species (and thus the encoded compomer) will differ from that of the other species in the library. The figure also illustrates that in certain preferred embodiments, the resulting compomers may be engineered to contain mass-modified subunits (representatively illustrated here by methylated C residues, "$C^{me}$").

FIG. 10 illustrates a class of target detection reagents wherein the target binding moiety comprises an antibody, which antibody is linked to the compomer template. Such linkage can involve a linker, and is preferably covalent. Also shown are embodiments wherein the target detection reagent encodes one (panel B) or two (panel C) primer binding sites, which sites can be used to amplify the compomer templates adjacent thereto before generation of the encoded compomers (or cleavage substrates).

DETAILED DESCRIPTION

Figure 8:
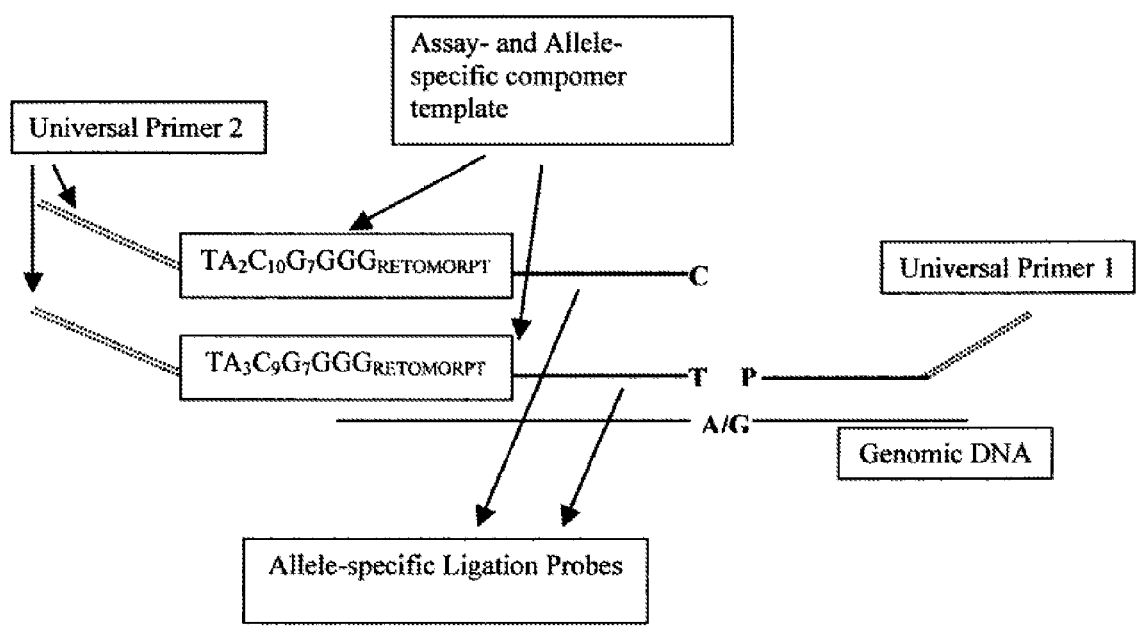
FIG. 8 depicts a set of target detection reagent species according to the invention, each of which comprises a first and second oligonucleotide. As shown in this example, two species of first oligonucleotide can be used to distinguish a single nucleotide transition (i.e., the difference between A or G at a particular nucleotide position in a target nucleic acid) in a genomic DNA. Which allele (containing A or G), or alleles, is present in a given sample can be determined by joining the 5' subunit of the second oligonucleotide to the 3' subunit first oligonucleotide that is complementary to either the A- or G-containing allele. When the first and second oligonucleotides are joined (e.g., by ligation), resulting the target detection reagent can be amplified by using a universal primer pair that is complementary to the primer binding sites (designated "Universal Primer 2" and "Universal Primer 1") present in the target detection reagent.
Figure 9A:
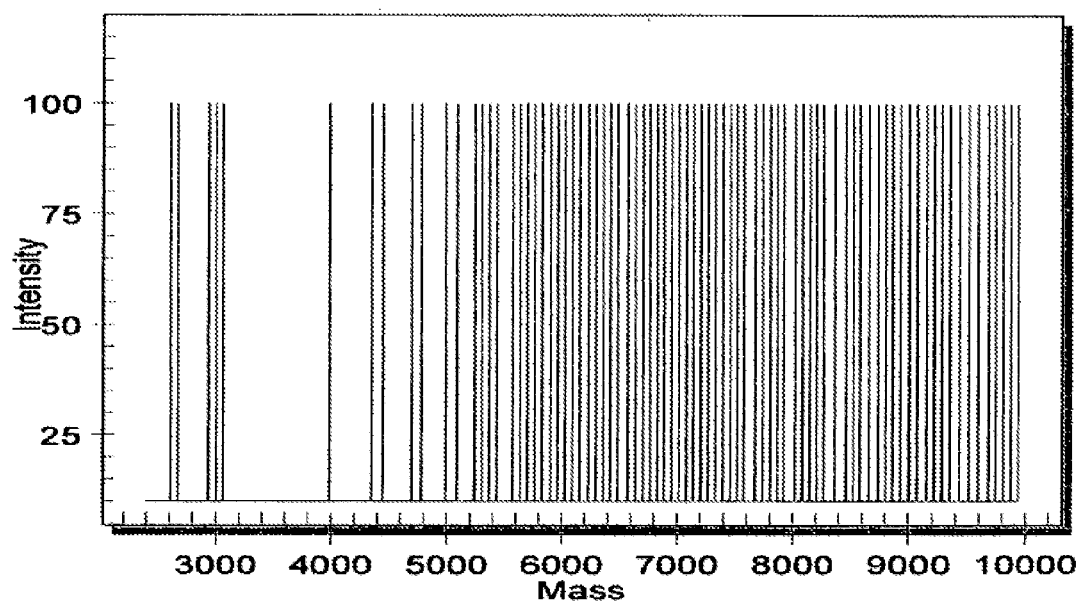
FIG. 9A shows simulated mass spectrum that may be obtained by detecting compomers generated in an assay according to the invention using, for example, linear axial TOF mass spectrometry. As shown in this representative example, 85 readily distinguished compomers (the formulas, lengths, and masses of which are shown in FIG. 9B) can be synthesized from ribonucleotides having a normal, or natural, isotopic distribution. The compomer species represented in this exemplary library can be represented by the formula: $(rA_x rG_y)_z rC_1$, where z is between 3-30 and z=x+y. These compomer species comprise either or both rA and rG subunits, and each species includes a cleavage base (here, a single rC at the 3'-terminus of each compomer, which cleavage can, for example, be accomplished by RNase A digestion). RNA-based compomers such as those depicted in this example can be generated, for instance, by transcription of the corresponding cleavage templates in an in vitro transcription reaction. As indicated, the 85 member compomer library illustrated here was designed for detection by linear axial TOF mass spectrometry using a mass window of 2500 Da to 10000 Da, with a mass resolution ($m_r$) of 450 at 1500 Da, 650 at 4000 Da, and 850 at 6000 Da. In designing the library, salt adduct positions (Na and K) were considered, and the library was engineered to exclude compomers having salt adducts with masses similar enough to other compomer species that misinterpretation of the results could occur. Doubly charged mass signals were also considered, and compomer species having potentially confounding masses due to this were also excluded from the library during the design phase.

Broadly, the instant invention provides methods for indirectly detecting one or more particular target molecule species, such as a particular polypeptide or nucleic acid species, in a sample, e.g., a biological sample. A particular species of target molecule is indirectly detected by detecting a compomer that is specifically correlated with the target molecule species. Compomers are linear polymers comprised of subunits, particularly nucleobase subunits, and they are generated from templates linked to target-specific molecules that specifically bind to the target molecule. To facilitate parallel analysis of multiple target molecule species in a single assay, compomer species are designed to be distinguishable from one another. Separate recognition is provided through one or more defined characteristics, which characteristics differ between compomer species. Compomer characteristics that may be defined include molecular mass, subunit sequence and length, and structure, as well as any other molecular characteristic that can be engineered to provide distinction between different species. Depending on the particular defined characteristic(s) of the compomers, a suitable system is employed for compomer detection.

The compomers of the present invention are useful for indirectly detecting the presence of a wide variety of target molecules, with biomolecular targets being particularly preferred. Representative examples of biomolecules whose presence in a sample can be signaled by a compomer include detection of gene sequences, alleles, allelic variations, non-coding nucleotide sequences, mutations within a gene or protein sequence, metals, toxins, polypeptides, carbohydrates, and lipids.

The following description begins with a discussion of representative sample preparation techniques, followed by a non-limiting and representative detailed description of the reagents and methods of the invention.

A. Samples; Sample Preparation

This invention provides for the efficient, simultaneous detection of one or more target molecules in a single sample. Samples that can be analyzed according to the invention include environmental samples, which may or may not include biological material. Particularly preferred samples are biological samples known or suspected to contain biomolecule species of interest. Samples for analysis may be obtained from any suitable source. After obtaining a sample, it is processed using any suitable technique to make the target molecules to be detected, if present in the sample or an aliquot thereof, accessible for interaction with target detection reagents according to the invention.

In the context of biological samples that may contain one or more target molecules of interest, e.g., nucleic acid molecules, polypeptides, lipids, metals, toxins, and carbohydrates, samples can be obtained from any source known or suspected to contain the target biomolecule species to be detected. Such samples can be made of solid materials, such as tissue, cell pellets, and biopsies, as well as liquids. Samples of biological fluids include urine, blood, saliva, amniotic fluid, mouth wash, lymph, sweat, sputum, mucous, tears, etc. Biological samples also include those taken from cell cultures, etc.

Biological samples can be obtained from any living or dead organism. Representative examples include plants and animals, as well as cells and tissues derived therefrom. It is envisioned that the instant invention will find particularly broad application in human and animal medicine.

Biological samples can be prepared for analysis using any suitable procedure, if desired. For example, freeze-thaw and alkaline lysis procedures can be useful for obtaining nucleic acid molecules from solid materials; heat and alkaline lysis procedures can be useful for obtaining nucleic acid molecules from cells in urine; and proteinase K extraction can be used to obtain nucleic acid from blood cells. Other suitable procedures are known in the art and can readily be adapted for use in the practice of this invention depending on the species of target molecules to be detected and the type of sample to be obtained. If desired, one or more purification and concentration steps can be employed in the sample preparation process to initially purify and/or concentrate the class(es) of target molecules to be detected. For example, nucleic acids can be isolated from cellular debris by precipitation using any of a number of suitable reagents known in the art. Other cellular components can be isolated using suitable fractionation procedures.

To obtain a sufficient quantity of target molecules, particularly target nucleic acid molecules, for analysis, it may be desirable to perform an initial amplification may be necessary. Examples of appropriate amplification procedures for use in the invention include: cloning (see, e.g., Sambrook, et al., *Molecular Cloning: A Laboratory Manual*, Cold Spring Harbor Laboratory Press, 1989), polymerase chain reaction (PCR) (see, e.g., C. R. Newton and A. Graham, PCR, BIOS Publishers, 1994; U.S. Pat. Nos. 4,683,195; 4,683,202; 4,800,159; 4,965,188; 5,468,613; 5,604,099; 5,656,493; 6,040,166; and 6,514,736), ligase chain reaction (LCR) (see, e.g., Wiedmann, et al., (1994) *PCR Methods Appl.*, vol. 3:57-64; Barnay, F. (1991), *Proc. Natl. Acad. Sci. USA*, vol. 88:189-93; U.S. Pat. Nos. 5,869,252 and 6,368,801), strand displacement amplification (SDA) (see, e.g., Walker, et al. (1994), Nucleic Acids Res., vol. 22:2670-77; U.S. Pat. No. 5,455,166) and variations such as RT-PCR (see, e.g., Higuchi, et al. (1993), Bio/Technology, vol. 11:1026-1030), allele-specific amplification (ASA), amplification by Q-beta replicase (Lizardi, et al. (1992), Bio/Technology, vol. 6:1197-1202), and transcription based processes (see, e.g., U.S. Pat. Nos. 5,480,784; 5,824,518; 6,087,133; and 6,214,587).

To facilitate analysis, target molecules may be immobilized to a solid support, although solution-based methods are preferred. Examples of appropriate solid supports include beads (e.g., silica gel beads, controlled pore glass beads, magnetic beads, Sephadex/Sepharose beads, cellulose beads, etc.); coated and uncoated nano particles; flat surfaces or chips (e.g., glass fiber filters, glass surfaces, metal surfaces (e.g., steel, gold, silver, aluminum, copper, etc.), capillaries, plastic (e.g., polyethylene, polypropylene, polyamide, polyvinylidenedifluoride membranes, and microtiter plates)); or pins or combs made from similar materials comprising beads or flat surfaces or beads placed into pits in flat surfaces such as wafers (e.g., silicon wafers).

Target molecule immobilization is preferably performed when it is desired or necessary to remove target detection reagents from an assay that have not bound to a target molecule for which they are specific prior to compomer (or cleavage substrate) synthesis. In preferred embodiments, target molecules are immobilized on a solid support using suitable capture reagents. For example, capture reagents suitable for use in the context of nucleic acid-based target molecules include oligonucleotides bound to a solid support. Preferably, such oligonucleotides hybridize to the target nucleic acid molecules in a region near the target nucleotide sequence. After nucleic acid molecules are captured, one or more target detection reagent species can be added to the reaction. Those that hybridize to their respective target sequences are retained, while those that do not hybridize may be washed away. Thereafter, compomers can be generated and detected.

B. Target Detection Reagents

Target detection reagents are used to detect target molecules of interest that are present in a sample. Target detection reagents are synthetic molecules that include a target binding moiety and a compomer template (or its complement), as shown in FIG. 1. Target binding moieties and compomer templates can be synthesized in a single reaction, or they may be joined by combining two or more subunits synthesized in different reactions. In preferred embodiments, target binding moieties and compomer templates are synthesized separately, after which they may joined when and as desired. The orientation of the compomer template and target binding moieties relative to each other is left to the discretion of the skilled artisan, and will depend on the particular application. Representative orientations for target detection reagents comprised of nucleic acid components include those wherein the compomer template is disposed 5' or 3' to the target binding moiety. Similarly, other optional components, e.g., primer binding sites (or complements thereof) may be included and disposed upstream or downstream (e.g., 5' or 3', respectively, in the case of nucleic acid-based components) of a target binding moiety and/or compomer template.

Because compomers are independent of the sequence or structure of a target molecule, a single library of compomer templates (or a subset thereof) that produce compomers optimized for detection by a particular detection system (e.g., MALDI mass spectrometry) can be linked to many different types of target binding moieties, for example, those made from nucleic acids and polypeptides (e.g., antibodies and antibody fragments). As will be appreciated, a compomer template may be directly linked to a target binding moiety. Alternatively, the compomer templates and target binding moieties can be linked through a linker. Preferably, the compomer template-target binding moiety linkage is covalent, although non-covalent linkages mediated, for example, by high affinity binding pairs (e.g., streptavidin and biotin, antibody and antigen, receptor and ligand, etc.) may also be employed.

Target binding moieties contain one or more a reactive groups, each of which is specific for a particular species of target molecule (e.g., a particular allele or polypeptide), although two reactive groups may be specific for the same target molecule, albeit to different regions. For example, different antibodies may be raised against the same polypeptide, with each different species being directed against a different epitope. Alternatively, two oligonucleotides that independently target different regions of the same gene, for example, to different alleles or different regions within the same allele, can be combined. In the context of nucleic acid detection, preferred target binding moieties are oligonucleotides specifically reactive with, and thus are capable of selectively hybridizing to, target nucleic acid sequences in the target nucleic acid molecules of interest. In addition to peptides, polypeptides, nucleic acids, and the like, other target binding moiety classes include aptamers and small molecules.

With regard to detecting non-nucleic acid target molecules, the target detection reagent typically contains at least one reactive group that comprises a polypeptide, preferably an antibody, an antibody fragment (i.e., the antigen-reactive portion), a receptor, a ligand for a target molecule that is a receptor, or a target-specific polypeptide derived from phage display-based procedure. Such polypeptide-based target binding molecules may be obtained from any suitable source organism, and they can be synthesized using any suitable technique. Particularly preferred are target binding moieties derived from the same plant or animal species as the target molecule to be detected. Also, for polypeptides containing more than about 25 amino acid residues, such molecules are preferably synthesized using recombinant techniques, while shorter polypeptides are preferably synthesized using a solid state chemistry.

In other embodiments, particularly those where the target molecule is a nucleic acid, or a polypeptide that specifically binds nucleic acids containing a specific nucleotide sequence, the reactive group of the target detection reagent comprises a nucleic acid molecule (e.g., an oligonucleotide) that specifically targets a target nucleotide sequence in the target nucleic acid molecule or, in some embodiments, a nucleic acid binding protein. In some embodiments, the target binding moiety is comprised of two molecules that specifically bind adjacently to each other in the target nucleotide sequence of the target molecule. Preferably, the molecules bind to the target such that the 3'-terminal nucleotide of one molecule is juxtaposed to the 5'-terminal nucleotide of the other molecule such that they can be linked, preferably by a ligase enzyme, to form a single molecule that comprises the target binding moiety of the particular target detection reagent.

Regardless of the reactive group(s) (i.e., the target binding moiety(s)) included in a given target detection reagent, the reagent also includes at least one compomer template. A compomer template, or its complement, minimally encodes compomer that can be generated under suitable conditions. In certain preferred embodiments, compomer templates encode a transcription unit that can direct the expression of the encoded compomer, e.g., by transcription, in embodiments where the compomer comprises ribonucleotides, or transcription and translation, as is the case when a compomer is comprised of amino acid residues. In other embodiments, the compomer template serves as the template for later compomer synthesis, for example, by primer extension.

Preferably, the compomer template is a single-stranded nucleic acid, typically an oligonucleotide, that comprises an engineered sequence of nucleotides, nucleosides, or other nucleobase-containing monomeric subunits. If desired, however, the compomer template can be a double-stranded molecule, in which case the methods and reagents employed are adapted accordingly. As will be appreciated, non-enzymatic approaches can also be used to generate compomers from a compomer template, in which event the components of the compomer template need not be engineered to provide the capacity for transcription by an RNA polymerase.

In preferred embodiments where the compomer template encodes a transcription unit, the transcription unit minimally encodes a promoter region and a compomer encoding region. Transcription from the transcription unit results in the production of a compomer, or an mRNA molecule that can be translated to generate an amino acid-based compomer. The compomer-encoding region of a transcription unit may, in some embodiments, code for one or more additional nucleotides in addition to that comprise the compomer (or an RNA molecule that can be translated to generate the compomer). Such larger precursor molecules, or cleavage substrates, can then be chemically or enzymatically treated to release the particular compomer.

In embodiments where compomers are synthesized as part of cleavage substrates, the larger precursor is engineered to facilitate the subsequent release of the compomer, for example, by chemical, physical, or enzymatic cleavage. While compomer release can be accomplished by any suitable method, it is currently preferred that the one, several, or many compomer species be simultaneously released by treating the reaction with one or more reagents (preferably a single reagent species) that specifically cleaves the cleavage substrate species at or within a subunit outside of the compomer portions of the larger precursors. As will be appreciated, the cleavage group may be any labile group that provides for release of a compomer from a cleavage substrate. The cleavage group may thus be a chemically cleavable linkage or labile chemical linkage and it may be positioned at either or both ends of a compomer. Such linkages may typically be cleaved by methods that are well known to those of skill in the art, such as by acid, base, oxidation, reduction, heat, light, or metal ion catalyzed, displacement, or elimination chemistry. Of course, cleavage may also occur at a subunit that includes groups or linkages cleavable by an enzyme. Enzymatically-cleavable release groups include phosphodiester or amide linkages as well as restriction endonuclease recognition sites.

In the case of single-stranded polynucleotide-based cleavage substrates, compomer cleavage can be accomplished, for example, by including one or more cleavable nucleobase subunit species not present in the compomer portion elsewhere in the cleavage substrate. After generation of the cleavage substrate, treatment with the cleavage reagent cleaves the subunit(s) intended to react with cleavage reagent to generate compomer species of the expected mass. The particular conditions required for cleavage will depend on the particular cleavage reagent employed. In the context of single-stranded compomers comprised of nucleotides, suitable cleavage reagents include those that provide for nucleotide-specific cleavage. Examples of such chemicals include those used in Maxam and Gilbert sequencing techniques (*Proc. Nat'l Acad. Sci. USA*, vol. 74(2):560-564, 1977), such as dimethylsulfate, hydrazine, and piperidine. Alternatively, modified nucleobase subunits (e.g., those containing methylphosphonate groups) susceptible or resistant to cleavage (be it chemical, enzymatic, or physical) may be employed.

If one or more compomers are designed as double-stranded nucleic acids, on the other hand, other methods of cleavage may be preferable. For example, a one or more restriction endonuclease cleavage recognition sites can be incorporated in the cleavage substrate. Particularly preferred are sites for type II restriction endonuclease, particularly those that comprise a four base-pair palindrome and which result in blunt-ended cleavage products. In embodiments where cleavage by a restriction enzyme results in a single-stranded overhang, an exonuclease may be used to remove the unpaired nucleotide(s).

In the context of preferred single-stranded compomers and cleavage substrates comprised of nucleobase-containing subunits, it is preferred that the compomer species (be there one, several, or many different compomer species synthesized in the particular reaction vessel as part of larger cleavage substrates) to be detected not contain the cleavable nucleobase subunit species. As will be appreciated, when a plurality of different compomers are generated, it is preferred that none of the compomer portions include a cleavage subunit. In this way, only the cleavable nucleobase subunit species will be cleaved in the cleavage reaction, thereby liberating the compomers. Moreover, only one cleavage reagent needs to be used to effect release of all of the various compomer species incorporated in the cleavage species. Preferred cleavable nucleobase subunit species include adenine, cytosine, guanine, hypoxanthine, orotic acid, thymine, uracil, and xanthine, and inosine. When one or more of nucleobase subunits is incorporated into a cleavage substrate, they may be cleaved by treatment with any suitable chemical, enzymatic, or physical technique under conditions known in the art. In a particular embodiment, the chemically cleavable linkage comprises a modified base, a modified sugar, a disulfide bond, a chemically cleavable group incorporated into the phosphate backbone of nucleic acids synthesized from nucleotides, or another suitable chemically cleavable linker. Chemically cleavable groups that may be incorporated into phosphate backbones are well known, and include dialkoxysilane, 3'(S)-phosphorothioate, 5'-(S)-phosphorothioate, 3'-(N)-phosphoroamidate, or 5'-(N)-phosphoroamidate. In further embodiments the chemically cleavable linkage may be a modified sugar, such as a modified ribose moiety.

With regard to compomers and cleavage substrates comprised of non-nucleobase-containing subunit species, the methods of the invention are adapted accordingly. For instance, in embodiments where cleavage substrates comprised of amino acids are generated (i.e., by translating a corresponding mRNA synthesized from one or more suitably designed transcription units), compomers can be released by suitable chemical or enzymatic cleavage in a process akin to the removal of peptide-based affinity tags from fusion proteins. The particular cleavage system used will depend on the particular cleavage desired. For example, in some embodiments, a cleavage reagent can be used specifically cleave an amino acid species not included in the compomer portion of the cleavage substrates present in the reaction. Alternatively, a site for cleavage by a specific exo- or endopeptidase can be designed into the cleavage substrate. Sites for cleavage by a particular endopeptidase cleavage typically comprise a short, unique amino acid sequence. Any site- or sequence-specific protease may be used for this purpose, and the reagents of the invention can readily be adapted for the use of such proteases in practicing the instant methods through the incorporation of the appropriate recognition site for the cognate protease. For example, systems employing the recombinantly expressed and purified catalytic subunit of bovine serine protease enterokinase have been reported (see, e.g., the website of Stratagene Cloning Systems, Inc.), where EK treatment cleaves a fusion protein immediately after the C-terminal residue of the enzyme's five-residue cleavage site to produce a protein having a native sequence. Accordingly, the EK recognition site can be engineered into a cleavage substrate such that the site's C-terminal amino acid residue immediately precedes the first amino acid residue of the compomer. Because the mass of the cleaved recognition site (and any additional amino acid residues that may precede the N-terminal amino acid of the cite) is known, a signal in a resulting mass spectra corresponding to the site will be readily detectable. In reactions where multiple compomer species are synthesized and each has such a cleavage site, only a single peak in the resulting spectra will be attributable to the cleaved non-compomer fragment.

The invention also includes embodiments wherein a target detection reagent further comprises a tag (e.g., biotin or digoxigenin) capable of being immobilized on a solid support, for example, the surface of a reaction vessel or a bead or particle in solution. Generally, the tag is capable of attaching to or being bound by a compound linked to the solid support. The tag may be attached to the target detection reagent directly, for example, by a chemical linkage between the tag and the solid support, or by a linker molecule disposed between the tag and the solid support. Tag molecules can bond covalently or non-covalently to the solid support, depending on the tag molecule used.

The invention also envisions mixtures containing more than one target detection reagent targeted for a particular region of a particular genetic locus or polypeptide. In this way, which of two or more genetic alterations at a particular nucleotide position in a particular gene, for example, can be detected in a single reaction as each variant will have a different compomer correlated with it. Similarly, if the genetic variation results in polypeptides having variant structures, such variations may be detected, for example, using different antibody (or antibody fragment) species each specific for only one of the variants. To facilitate the construction of such target detection reagents, it may be desirable to synthesize the target binding moiety in segments, particularly in embodiments where the target molecule is a nucleic acid. When synthesized in fragments, one fragment may be invariant, in that that portion of the target binding moiety is common to all of the potential variants. The other segment, which may be as small as a single nucleobase-containing subunit, provides for variant discrimination.

Similarly, different target detection reagents can be targeted to different regions within a particular gene. For example, if is known to possess several different SNPs at different locations, it may be desirable to produce one or more target detection reagents specific for each SNP position.

While less preferred, the invention also envisions mixtures wherein a single compomer template species is linked two or more different target binding moieties. As a result, detection of the compomer indicates that one of the several targets was present in the sample. If desired, which of the target molecules was, in fact, present can be determined in a subsequent assay. Alternatively, if a plurality of different compomer species are detected, each of which correlates with one or more different target molecules, the presence or absence of at least some of which are correlated with the presence or absence of other target molecules that can be detected in the assay, various statistical methods known in the art may be used to determine which target molecules are indeed present in the sample being analyzed.

For particular embodiments, synthesis of target detection reagents, and the components thereof (e.g., target binding moieties and compomer templates), is performed using solid state synthetic methods, which allows for a wide variety of compounds to be produced using combinatorial methods. In such embodiments, target binding moieties and compomer templates can be synthesized by repeating the step of adding an activated subunit (e.g., an activated nucleoside monomer species or an activated amino acid species) under conditions to allow for polymerization of a growing nucleic acid or polypeptide as many times as necessary to synthesize the desired molecular species. After completing the synthesis of the target binding moieties and compomer templates, they can be linked together. Such linkages may be direct, in that one end of the linear compomer template is linked directly to the desired target binding moiety using a suitable chemistry. Alternatively, the linkage may be indirect, such that a linker molecule is used to covalently attach a compomer template to the desired target binding moiety, either simultaneously or sequentially. The linkage of a linker to a compomer template may the same or different than used to link the linker to the target binding moiety. Any desired linker may be employed. Preferred linker molecules include aliphatic chains comprising from 1 to about 100 or more carbon atoms. While target binding moieties and compomer templates are preferably covalently linked, the linkages may also be non-covalent, in which event they are preferably formed by the members of a high affinity binding pair. In embodiments where a target detection reagent comprises a target binding moiety and a compomer template assembled from subunits that can be polymerized using compatible chemistries (e.g., nucleobases polymerized using the same backbone chemistry), it is often preferred to synthesize the complete target detection reagent in a single series of reactions.

C. Methods of Target Detection

The invention further provides methods for detecting specific target molecules. Such methods include the steps of: (a) obtaining a target-specific target detection reagent that comprises a target binding moiety and a compomer template; (b) contacting a sample known or suspected to contain the target molecule with the target detection reagent to produce reagent: target complexes; (c) generating a compomer (or cleavage substrate, as the case may be) from the compomer template; and (d) using a detection technique suitable for detecting the compomer species generated in the assay and thereby indirectly detect the target molecule correlated with the particular compomer species. Such methods can be performed for single target molecule species, small groups of different target molecule species, and large numbers of different target molecule species in multiplex formats, for example, to detect one or more of several compomers each correlated with the same target molecule, to detect one or more compomer species each of which is correlated with two or more different target molecule species, and to indirectly detect a plurality of different target molecule species by using a library of compomer species, each of which is correlated with only one target molecule. As will be appreciated, different compomers can be used to simultaneously detect tens, hundreds, and even thousands of different target molecule species (e.g., target nucleic acids) in a single assay.

Libraries of compomer species may be designed for use in a variety of different assays, or to indirectly indicate the presence of different target molecules. For example, in some embodiments, the compomers of the invention are used in the analysis of patient samples to detect the presence of one or more intraspecies genetic variations. In other embodiments, the same compomer library, encoded by the same compomer templates, are linked to different target binding moieties, for example, target binding moieties that specifically bind to nucleic acids or polypeptides from other species, e.g., pathogens known to infect a particular host species. Alternatively, the compomer templates can be linked to target binding moieties that target biomolecules other than nucleic acids, for example, carbohydrates, lipids, proteins or polypeptides.

Compomer libraries can be engineered to be of any suitable size, and will comprise at least two different compomer species (as, of course, will the compomer templates encoding the compomers or cleavage substrates). The upper boundary on library size will limited factors such as the resolution of the detection system employed, the availability of isotopically defined subunits (in certain instances where mass discrimination is used to distinguish compomer species), and the incremental differences between the species comprising the library. Clearly, for large scale multiplexing, it is preferred that the target detection reagents provide for the generation of many different compomer species.

Thus, the present invention concerns methods for detecting a target molecule, often many different target molecule species, in a single reaction. Generally, such multiplex methods involve obtaining a plurality of target detection reagents according to the invention. In most embodiments, each target detection reagent species includes a target binding moiety and a compomer template that encodes a template that allows for the direct or indirect generation of a compomer correlated with the particular target molecule targeted by the target binding moiety. Direct generation of a compomer or cleavage substrate occurs by using the compomer-encoding (or cleavage substrate-encoding) portion of the compomer template as a guide for the chemical or enzymatic generation of the encoded compomer (or cleavage substrate). In some preferred embodiments, compomer or cleavage substrate generation results from transcription of a transcription unit carried in the compomer template by a suitable RNA polymerase to generate a compomer (or cleavage substrate containing a compomer). In other embodiments, a short primer becomes hybridized to a complementary region of bases in the compomer template, after which it is extended, for example, in a primer extension reaction wherein extension is catalyzed by a suitable polymerase. Indirect compomer generation, on the other hand, refers to the inclusion of one or more intermediate steps between, for example, the transcription step and generation of the compomer (or cleavage substrate). As an example, in embodiments where a compomer is encoded within a transcription unit of a compomer template, the mRNA transcripts generated from the transcription unit may be translated into specific polypeptides, which may or may not require further processing (e.g., cleavage, as may be desired in instances where the initial polypeptide is a cleavage substrate that must be further processed to release the compomer contained therein).

As those in the art will appreciate, when the target molecules are nucleic acid molecules, it may be desirable to amplify portions of the nucleic acids in order to increase the representation of the target molecules in the sample prior to compomer generation. Any suitable amplification procedure can be employed using primers that specifically allow amplification of the target molecules being sought. Before, although in some embodiments after, amplification, target detection reagents specific for the particular target molecules sought to be detected are included in the reaction. In other embodiments, amplification of target regions is mediated by components of the target detection reagents themselves, typically by inclusion of one or more primer binding sites in the target detection reagent. Preferably, primer binding sites flank, or are outside of the, the compomer template portion of the target detection reagent. Preferably, primer binding sites are engineered to be either 5' or 3' to the compomer template of the particular target detection reagent. In particularly preferred embodiments, at least two different primer binding sites (one actually being complementary to a first primer, the other being the complement of a second primer that can hybridize to the strand extended from the first primer) are included in a target detection reagent.

For example, as illustrated in FIG. 8, in certain preferred embodiments a target detection reagent comprises two or more portions that must be joined in order for compomers to subsequently be generated. As shown in FIG. 8, two different target detection reagents may be generated from three different oligonucleotides. Two of the oligonucleotides (each a "first" oligonucleotide) are allele-specific, and allow a single nucleotide difference (A or G) at one nucleotide position to be distinguished due a difference in the 3' terminal nucleobase of each first oligonucleotide (a "T" in one and a "C" in the other). The other oligonucleotide (the "second" oligonucleotide) is not allele specific, and is designed to contain a target binding moiety portion that is substantially complementary, and preferably perfectly complementary, to a portion of the target sequence. Upon hybridization of the first and second oligonucleotides, juxtaposition of one of the two first oligonucleotides (i.e., the one having a 3' terminal nucleobase complementary with the nucleotide present in the particular target molecule) with the second oligonucleotide allows the first and second oligonucleotides to be joined (preferably by a ligation reaction) to form a complete target detection reagent. Given that, as shown in the embodiment in FIG. 8, the first and second oligonucleotides are flanked by universal primer binding sites, the particular target detection reagent species (and others that may be present in the reaction that include the same primer binding sites) can subsequently be amplified to yield substrates that can be used for cleavage substrate (or compomer) generation by RNA polymerase-mediated transcription from the promoter.

As will be appreciated, in embodiments of target detection reagents that include two primer binding sites (meaning a primer binding site for a first primer and the complement of a the primer binding site for a second primer), one, and preferably both, sites are engineered to bind a universal primer, particularly when intended for use in multiplex assays. In some embodiments where a primer pair is used to amplify some or all of a target detection reagent following the reagent's interaction with the biomolecule targeted thereby, it may be desirable to employ primer binding sites wherein one site binds to a universal primer while the other site is specific for the particular target detection reagent species. While less preferred, it is also understood that the invention encompasses embodiments wherein the primer binding sites are not targeted by universal primers, but instead are targeted by primers specific for the particular target detection reagent species. In addition, target detection reagents can be engineered to include more than two primer binding sites, thereby facilitating amplification of different portions of the reagent using different primers.

Thus, in preferred embodiments, after amplification, if performed, compomers (or larger precursors comprising compomers) can be generated from the compomer templates included in the one or more target detection reagent species included in the reaction. Methods of generating a compomer are provided, and comprise combining subunits, e.g., nucleobase-containing subunits (e.g., nucleotides), amino acids, sugar moieties, etc., of the same or different subunit species under conditions that allow for polymerization. Typically, nucleotides are polymerized by a polymerase, while oligonucleotides are polymerized by a ligase. Particularly preferred methods are those where compomers or cleavage substrates are generated from transcription units in a corresponding compomer template using an enzyme. Especially preferred enzymes for polymerizing ribonucleotides are RNA polymerases, particularly T7, T3, and SP6 RNA polymerases, although other RNA polymerases can be used, provided that the compomer template encodes a suitable promoter. When compomers or cleavage substrates are made of amino acid residues, preferred synthesis methods are also enzymatic. Preferred are in vitro translation methods, where mRNAs transcribed or otherwise generated from the corresponding transcription units are translated into polypeptides. Primer extension methods may also be employed to generate compomers and cleavage substrates. It is also contemplated that other methods of polymerizing subunits can be employed, be they monomeric subunits or pluralities of monomeric subunits assembled into precursors for subsequent assembly into larger units, up to and including compomers, cleavage substrates, transcription units, compomer templates, oligonucleotides, etc. Thus, in other embodiments, compomer polymerization is mediated by chemical synthesis. In the context of nucleic acid- or amino acid-based compomers, the preferred synthetic methods are essentially those for standard synthetic nucleic acid and peptide synthesis, respectively. In further embodiments, nucleobase subunits, such as nucleotides included in a compomer, may have a chain terminating modification. For example, an added nucleotide may be a chain terminating dideoxy nucleotide, thereby preventing the addition of other nucleotides. In other embodiments, a subunit added to a compomer may contain a nuclease-blocking moiety to prevent digestion of the compomer or cleavage substrate by a nuclease, such as ribonuclease.

As described above, each compomer species has a defined characteristic that allows it to be distinguished from other compomer species that may be generated in a given assay. Taking mass to be the defined characteristic, for example, each compomer species will be engineered such that when it is generated in an assay it will have has a unique mass or mass range that allows is to be resolved from the other potential compomer species by the mass detection system used in the particular analysis. As a result, detection of a compomer correlated with a particular target molecule indirectly indicates that the target molecule targeted by the target binding moiety of the target detection reagent is present in the sample being assayed.

In the methods of the invention, a sample known or suspected to contain the target molecule(s) of interest are contacted with one or more target detection reagent species under conditions suitable to allow for the formation of reagent: target complexes. If desired, and is the target detection reagent has been designed to be, or is otherwise capable of being, amplified, the target detection reagents that form reagent:target complexes may be amplified using a process compatible with the particular target detection reagent design. Compomers or cleavage substrates may then be generated, after which an aliquot of the reaction may be subjected to a detection technique capable of distinguishing compomer species based on the defined characteristic engineered for this purpose. A particularly preferred defined characteristic is mass, and preferred methods for distinguishing compomer species, if any, based on mass is mass spectrometry, particularly MALDI-TOF mass spectrometry. Detection of a compomer species indicates that the target molecule correlated with the compomer was present in the sample.

As described elsewhere herein, more than one target molecules, including target nucleic acid molecule species, may be simultaneously detected in a particular sample. Indeed, different classes of target molecules, e.g., nucleic acids, polypeptides, lipids, carbohydrates, etc., may be indirectly detected in the same assay through application of the instant methods. Such "multiplexing" can be achieved by using different compomer species, wherein each compomer species preferably is uniquely correlated with a particular target molecule, such that detection of the compomer species correlated therewith indirectly signals that the target molecule was present in the sample being analyzed. The different compomer species can be distinguished in a single assay by virtue of the differences in the defined characteristic(s) of each compomer species. Taking mass differences as an example, sensitive mass analysis based on molecular weight differences can be used to distinguish between various compomer species. As will be appreciated, mass differences between compomers should preferably be large enough so that detection is possible in a single analysis. The differences in mass between different compomer species are sufficient to be resolved by the particular mass analysis platform (i.e., hardware and software) being employed. In the context of compomers, mass differences can be achieved either by the sequence (composition or length) of the compomer species, as well as by introducing mass-modifying moieties into one or more of the building blocks (e.g., ribonucleotides in the case of RNA-based compomers) used in the synthesis of the compomers. Examples of mass modifying moieties include, for example, a halogen (e.g., F, Cl, Br and/or I), an azido, or of the type, XR, wherein X is a linking group and R is a mass-modifying functionality. Also useful in the design of compomers of specific masses are nucleotides that are isotopically defined, in that one or more of the heavy atom species (i.e., N, C, O, etc.) present in a particular nucleotide species will be enriched for a particular isotope.

Without limiting the scope of the invention, in embodiments wherein mass is the defined characteristic, mass modifications of different increments can be introduced during compomer or cleavage substrate generation, preferably through the incorporation of mass-modified building blocks (e.g., ribonucleotides) into nascent compomers or cleavage substrates, particularly when two or more compomer species are to be generated concurrently such that their respective masses might be difficult to resolve. Mass increments may be uniform, as occurs when a single mass modifying moiety species is used to modify the masses of one or more of the different building blocks used to synthesis the compomers in a given assay. Alternatively, mass increments may be non-uniform, as can occur when different mass modifying moieties are used. Any suitable chemistry can be used to attach a mass modifying moiety to a compomer building block. For example, if oligo/polyethylene glycol derivatives having a mass-modifying increment of 44, five different mass-modified species can be generated by just changing using from 0 to 4 of these moieties. An oligo/polyethylene glycol can also be monoalkylated by a lower alkyl such as methyl, ethyl, propyl, isopropyl, t-butyl, and the like. Linking functionalities can also be used to link mass modifying moieties to one or more of the compomer building blocks. Of course, mass-modifying moieties other than oligo/polyethylene glycols can also be selected and attached via appropriate linking chemistries.

Because one or more particular target molecules are likely to be present in a given sample only in trace quantities, it is often preferred to amplify either the target molecule(s) or, even more preferably, the target detection reagents (or a portion thereof, i.e., the compomer template) prior to compomer synthesis. This ensures that a sufficient number of compomer molecules will be synthesized for subsequent detection in the event the corresponding target molecule is present in the sample.

In embodiments where the target molecule species are nucleic acids and it is desired to amplify the targets prior to exposure to the target detection reagents, any suitable nucleic acid amplification technique can be employed. One preferred method is polymerase chain reaction ("PCR") and its variants, while another preferred method is an isothermal, transcription-based amplification method. Regardless of the amplification method employed, amplification of each target (unless two or more targets comprise genetic variants in the same region of the same gene) typically requires the use of at least two distinct amplification primers. Thus, highly multiplexed reactions require the use of numerous different amplification primers pairs, which in many cases leads to differences in the amplification efficiency of one or more of the targets. For this reason, it is preferred that amplification reactions be performed after the sample has been contacted with the various target detection reagents used in the particular assay. Amplification is then performed using the reagent: target complexes that may, but need not, be isolated from the other components of the initial reaction prior to amplification. Because of this, those portions of the target detection reagents designed to be amplified (i.e., at least the compomer templates) can be amplified using as few as a single pair of amplification primers. In such cases, the primers are referred to as "universal primers," as they can be used to amplify all of the nucleic acids desired to be amplified in a particular multiplexed amplification. Moreover, the amplification reaction can be optimized for the particular universal primer pair designed for use in the particular assay in order to achieve efficient, high level amplification. As known to those in the art, the region of nucleic acid to be amplified is flanked by the binding sites (or their complements) for the amplification primers.

As described above, for multiplex reactions it is most desirable to use only a single pair of "universal" primers to prime the extension reactions in the amplification process. Thus, one primer pair can be used to amplify each of the different nucleic acid sequences bracketed by the primer binding sites. Of course, it is also possible to use more than one pair of primers, even as many as one or more primer pairs per different nucleic acid species to be amplified. In other embodiments, a single primer species may be used to prime the synthesis of the forward or reverse strand of a particular amplicon, in which event a binding site (or the complement thereof) is positioned to flank one end of each of the different nucleic acid species to be amplified. The other primer of the primer pair will be specific for the particular nucleic acid being amplified. As such, in such embodiments each primer pair will comprise a universal primer and a primer specific for the particular nucleic acid. If desired, an amplification primer may also contain a functional group capable of being immobilized on a solid support, such as biotin or digoxigenin. Resulting amplicons can then be isolated from other reaction components, if desired.

As described elsewhere herein, the methods of the invention are preferably used in multiplex formats. In preferred examples of such formats, each target molecule to be detected correlates with a different compomer species, i.e., each compomer uniquely identifies a particular target molecule in the particular assay. As such, as compared to each other, each target detection reagent species comprises a different target binding moiety and a different compomer template. Thus, the subsequent detection of the particular compomer indirectly indicates the presence in the sample of the target molecule with which the compomer was correlated.

Of course, in addition to such one target/one compomer embodiments, others are also envisioned. For example, the invention also envisions embodiments wherein a sample containing one or more target molecule species is contacted with a plurality of target detection reagents, two or more one of which comprise a compomer template encoding the same compomer species for the target molecule species. Thus, the subsequent detection of a particular compomer species indicates that one or more of the several targets correlated with the compomer was present in the sample being tested. Such results may be deconvoluted by further experimental or statistical analysis to determine which target molecules were present in the sample. In other embodiments, the methods involve testing a sample by using a plurality of different target detection reagents for a particular target that differ not in their target binding moieties, but in their compomer templates. Accordingly, the target detection reagents target the same target molecule, and the subsequent detection of any, some, or all of the compomers correlated with the particular target indicate that the target was present in the sample.

D. Compomer Detection

Compomers can be detected using any detection process suitable for detecting the one or more compomer species that may be generated in a given assay, although the level of multiplexing possible in a given assay may vary. Representative examples of the detection systems that may be employed for this purpose include mass spectrometry, electrophoresis, chromatography, nucleic acid hybridization, and NMR. When the defined characteristic useful for distinguishing compomer species relates to mass, a particularly preferred detection is mass spectrometry; however, as those in the art will appreciate, other detection systems known in the art may be readily adapted for use in practicing the invention based on this specification. Given this, the following description focuses on mass, although it is understood that the scope of the invention is not limited to mass-based detection systems and techniques. Preferred mass spectrometer formats for use in the invention are electrospray (ES), matrix assisted laser desorption ionization (MALDI), ion cyclotron resonance (ICR), and Fourier Transform. For ES, the samples, dissolved in water or in a volatile buffer, are injected either continuously or discontinuously into an atmospheric pressure ionization interface (API) and then mass analyzed by a quadrupole. The generation of multiple ion peaks that can be obtained using ES mass spectrometry can increase the accuracy of the mass determination. Even more detailed information on the specific structure can be obtained using an MS/MS quadrupole configuration. In MALDI mass spectrometry, various mass analyzers can be used, e.g., magnetic sector/magnetic deflection instruments in single or triple quadrupole mode (MS/MS), Fourier Transform, and time-of-flight (TOF) configurations. For the desorption/ionization process, any suitable matrix/laser combination can be used. Ion-trap and reflectron configurations can also be employed. Currently, MALDI-TOF mass spectrometry is most preferred. Mass spectrometry and other methods of detecting compomers are described, for example, in U.S. Pat. Nos. 5,118,937; 5,202,561; 5,464,985; 5,547,835; 5,605,798; 5,622,824; 5,691,141; 5,777,324; 5,864,137; 5,869,242; 5,919,646; 5,922,542; 5,928,906; 6,024,925; 6,043,031; 6,051,378; 6,090,558; 6,104,028; 6,111,251; 6,194,144; 6,197,498; 6,207,370; 6,221,601; 6,221,605; 6,225,450; 6,235,478 6,238,871; 6,258,538; 6,268,131; 6,268,144; 6,277,573; 6,300,076; 6,322,970; 6,379,917; 6,387,628; 6,423,966; 6,428,955; 6,436,635; 6,440,705; 6,458,945; 6,468,748; 6,475,736; 6,500,621; 6,500,650; 6,558,902; 6,566,055; 6,566,059; 6,582,923; 6,589,485; 6,602,662; 6,610,492; 6,635,452; 6,660,229; 6,706,530; and 6,723,564, as well as commonly owned U.S. patent application Ser. Nos. 09/839,629 (publication number 20020155587) and 10/128,680 (publication number 20030033091).

Prior to mass analysis (e.g., by mass spectrometry), it may be useful to "condition" nucleic acid molecules to reduce the laser energy required for volatilization and/or to minimize fragmentation. Conditioning is preferably performed while a target detection site is immobilized. An example of conditioning is modification of the phosphodiester backbone of the nucleic acid molecule (e.g., cation exchange), which can be useful for eliminating peak broadening due to a heterogeneity in the cations bound per nucleotide unit. Contacting a nucleic acid molecule with an alkylating agent such as alkyliodide, iodoacetamide, β-iodoethanol, or 2,3-epoxy-1-propanol can transform the monothio phosphodiester bonds of a nucleic acid molecule into phosphotriester bonds. Alternatively, phosphodiester bonds may be transformed to uncharged derivatives employing trialkylsilyl chlorides. Further conditioning involves incorporating nucleotides with reduced sensitivity for depurination, such as N7- or N9-deazapurine nucleotides, or RNA building blocks or using oligonucleotide triesters or incorporating phosphorothioate functions that are alkylated or employing oligonucleotide mimetics such as peptide nucleic acids (PNAs).

E. Applications

The target detection reagents and the compomers they encode have a variety of uses. For example, target binding moieties can target particular known biomolecules, including proteins and nucleic acids. Especially preferred target molecules are those that are known to be associated with, if not the cause of, a particular condition such as a disease or disorder. After a target detection reagent specific for a target molecule binds to the target molecule, a compomer can be generated from the compomer template, after which it can then be detected using a compatible detection system, thereby indirectly indicating the presence of the particular target molecule.

In some embodiments, the methods described herein can be used, for example, to detect any known genetic variation, including any of the more than 4,000 currently known human heritable genetic diseases (e.g., hemophilias, thalassemias, Duchenne Muscular Dystrophy (DMD), Huntington's Disease (HD), Alzheimer's Disease, and Cystic Fibrosis (CF)). Certain genetic variations, for example, some SNPs, are known to be associated with a particular diseases. In addition to detecting SNPs and point mutations, some of which are correlated with, for example, the occurrence of or predisposition to a specific disease, no response or an adverse reaction to a particular drug, etc., other genetic variations can also be detected using the instant methods, including those that cause certain birth defects that result from chromosomal abnormalities, such as Trisomy 21, Trisomy 13, Trisomy 18, Monosomy X, and other sex chromosome aneuploidies such as Klinefelter's Syndrome. Still other genetic variations that can be detected in accordance with the invention include deletions, duplications, insertions, and rearrangements. Additionally, modifications (e.g., chemical modifications such as methylation) to genes and non-coding regions of chromosomes and extrachromosomal elements. Differences in RNA processing and gene transcription can also be studied using the instant methods.

Viruses, bacteria, fungi, and other pathogens contain nucleic acid sequences that can be distinguished from those of the host organism. Detecting or quantitating nucleic acid sequences or other biomolecules (e.g., proteins, enzymes, cell wall components, etc.) that are specific to an infectious organism can be important for diagnosing or monitoring treatment of an infection. Examples of disease-causing viruses that infect humans and animals include retroviruses (e.g., human immunodeficiency viruses, such as HIV-1 and HIV-2, and feline leukemia virus); picornaviruses (e.g., polio viruses, hepatitis A virus, entero viruses, human coxsackie viruses, rhinoviruses, and echoviruses; calciviruses (e.g., strains that cause gastroenteritis); togaviruses (e.g., equine encephalitis viruses, rubella viruses); flaviruses (e.g., dengue viruses, encephalitis viruses, yellow fever viruses); coronaviruses; rhabdoviruses (e.g., vesicular stomatitis viruses, rabies viruses); filoviruses (e.g., ebola viruses); paramyxoviruses (e.g., parainfluenza viruses, mumps virus, measles virus, respiratory syncytial virus); orthomyxoviruses (e.g., influenza viruses); bungaviruses (e.g., Hantaan viruses, bunga viruses, phleboviruses and Nairo viruses); arena viruses (e.g., hemorrhagic fever viruses); reoviruses (e.g., reoviruses, orbiviurses, and rotaviruses); bimaviruses; hepadnaviruses (e.g., Hepatitis B virus); parvoviruses; papovaviruses (e.g., papilloma viruses, polyoma viruses); adenoviruses; herpes viruses (e.g., herpes simplex virus (HSV) 1 and 2, varicella zoster virus, cytomegalovirus (CMV), herpes viruses); pox viruses (e.g., variola viruses, vaccinia viruses, pox viruses); iridoviruses (e.g., African swine fever virus); the agent of delta hepatitis; Hepatitis C virus; Norwalk and related viruses; and astroviruses.

Examples of infectious bacteria include: *Helicobacter pyloris, Borelia burgdorferi, Legionella pneumophilia*, various *Mycobacteria* species (e.g., *M. tuberculosis, M. avium, M. intracellulare, M. kansaii, M. gordonae*), *Staphylococcus aureus, Neisseria gonorrhoeae, Neisseria meningitidis, Listeria monocytogenes, Streptococcus pyogenes* (Group A *Streptococcus*), *Streptococcus agalactiae* (Group B *Streptococcus*), *Streptococcus* (viridans group), *Streptococcus faecalis, Streptococcus bovis, Streptococcus* (anaerobic species), *Streptococcus pneumoniae*, pathogenic Campylobacter species, *Enterococcus species, Haemophilus influenzae, Bacillus antracis, corynebacterium diphtheriae, corynebacterium* species, *Erysipelothrix rhusiopathiae, Clostridium perfringens, Clostridium tetani, Enterobacter aerogenes, Klebsiellapneumoniae, Pasturella multocida, Bacteroides species, Fusobacterium nucleatum, Streptobacillus moniliformis, Treponemapallidium, Treponema pertenue, Leptospira*, and *Actinomyces israelli*.

Examples of infectious fungi include *Cryptococcus neoformans, Histoplasma capsulatum, Coccidioides immitis, Blastomyces dermatitidis, Chlamydia trachomatis, Candida albicans*. Other infectious organisms (e.g., protists) include *Plasmodium falciparum* and *Toxoplasma gondii*.

Target detection reagents of the invention comprise a target binding moiety that is specific for the target biomolecule to be detected. As will be appreciated, the target binding moiety will depend on the target molecule to be detected. For example, when the target molecule is a nucleic acid molecule, it is preferred that the target binding moiety of the target detection reagent also be polynucleotide (e.g., a synthetic oligonucleotide or other molecule comprised of subunits capable of base-specific hybridization to the bases of the nucleotides comprising the targeted region of the target nucleic acid. Alternatively, in embodiments where the target molecule is a protein, a preferred molecular class from which suitable target binding moieties may be obtained are antibodies (or the antigen binding portions thereof).

As described above, certain preferred embodiments of the invention relate to the detection of specific target nucleic acid molecules. There are a variety of reasons for detecting a particular nucleic acid, including detection of infectious agents within a clinical sample, detection of an amplification product derived from genomic DNA or RNA or message RNA, detection of a gene (cDNA) insert within a clone, detection of methylation or other modifications to nucleic acid molecules, detection of differential mRNA splicing and/ or editing, etc. As will be appreciated, target nucleic acid detection may employ one or any combination of the methods described herein for the preparation of the target detection reagent and the release and detection of the encoded compomer. If desired, one may also quantify the amount of compomer detected, as may be the case in other embodiments of the invention as well, for example, detection of a target polypeptide using a target detection reagent which comprises a compomer template and a target binding moiety that comprises an antibody that is specifically reactive with the target polypeptide under reacting conditions. In the context of nucleic acid detection, most of these methods involve the use of a target-specific probe (i.e., target detection moiety) as a pre-requisite to the synthesis of the compomer (which is encoded by the compomer template of the target detection reagent that also includes the particular target detection moiety). In cases where only small amounts of target material may be present in a sample, or if only a small amount of sample is available, an amplification technique can be employed to increase the number of compomer templates.

As described above, an advantage to using target detection methods that employ compomers is the ability to simultaneously assay for the presence of many target molecule species. Due to broad overlapping spectrums produced by existing fluorescent chromophores, an upper limit for fluorescence multiplexing is most likely to be about ten different labels. With a MALDI-TOF mass spectrometer or direct laser-desorption mass spectrometer or an electrospray mass spectrometer, multiplexing of tens, hundreds, and even thousands of different compomers is possible.

Particularly preferred embodiments involve the detection of genetic variants such as single base polymorphisms, or SNPs, which generally requires a great deal of sensitivity. Such methods include detection of "hot spot" point mutations and identification of the base at known SNP sites. Target-specific probes can be prepared that hybridize to such sites. To ensure high fidelity, preferred SNP-specific target binding moieties are those that comprise two oligonucleotides that hybridize to adjacent regions of the particular target molecule. For example, one of the probes binds to a portion of the target such that its 3'-terminal nucleobase-containing subunit hybridizes only with the nucleotide corresponding to the particular SNP. The other oligonucleotide also hybridizes to the target, preferably such that its 5'-terminal residue can be ligated to the 3'-terminal residue of the first oligonucleotide. Oligonucleotides so hybridized to a target nucleic acid are said to be juxtaposed. In this way, one or more first oligonucleotides can be provided to distinguish the various polymorphism(s) at a particular nucleotide position in a target nucleic acid molecule, whereas the second oligonucleotide, while specific for its target sequence, it not specific for a particular genetic variation. Of course, embodiments than employ three or more oligonucleotides capable of hybridizing in juxtaposed positions on a target nucleic acid may also be used. Other embodiments involve oligonucleotides pairs (or larger groups) where a gap spanning one or more nucleotides results following hybridization of the oligonucleotides comprising the group. In such embodiments, a gap filling reaction can be performed to fill in the gap(s) and allow the oligonucleotides to be joined to form a substrate that can be used for compomer generation, preferably after amplification. Preferred SNP-detection embodiments encompass the multiplexing of a large number of different target detection reagents so as to detect many genetic variations (e.g., SNPs) simultaneously. Preferably compomers are be present to uniquely signal detection of one or more of the various variants that can be detected using the particular set, or library, of target detection reagents.

Depending on the circumstances of a particular assay, the methods of the invention can be preformed either pre- or post-natally, and may even be performed postmortem. The methods of the invention have a variety of applications in addition to merely detecting whether one or more particular target molecules are present in a sample, including individual genotyping and determining identity or heredity (e.g., paternity or maternity). As FIG. 8 shows, genetic variations at particular nucleotide positions can be assessed, including determining whether a particular diploid genome (if the relevant portion thereof is present in a sample) is homozygous or heterozygous for a particular allelic variation.

Another application concerns embodiments of the invention that relate to monitoring gene expression. In such embodiments, different target detection reagents are used to detect compomers representative of the genes being expressed in a particular cell culture and which are present in concentrations related to the mRNA abundance levels of the particular gene. The target nucleic acids typically comprise mRNA or first-strand cDNA, as well as amplified nucleic acid products. As such, the target nucleic acids should be present in concentrations related to their mRNA abundance levels. If desired, amplification may be used to selectively amplify a subset of the mRNA pool from a cell sample to increase the detection signal for those genes and to reduce the background from genes outside of the amplified subset. As with other methods of the invention, such methods typically employ a target detection reagent for each gene (or portion thereof) of interest, such that subsequent detection of a compomer species correlated with the particular target molecule indirectly indicates that the gene is being expressed in the sample.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

All patents and publications mentioned in the specification are indicative of the levels of those of ordinary skill in the art to which the invention pertains. All patents and publications are herein incorporated by reference to the same extent as if each individual publication was specifically and individually indicated to be incorporated by reference.

The invention illustratively described herein suitably may be practiced in the absence of any element(s) not specifically disclosed herein. Thus, for example, in each instance herein any of the terms "comprising", "consisting essentially of", and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

The invention claimed is:

1. A method for identifying the presence or absence of a target nucleic acid in a sample, which comprises:
  (a) contacting a sample with a target detection reagent that forms a reagent:target complex when target is present in the sample, wherein:
    (i) the target detection reagent comprises a transcription unit comprising a promoter region operatively linked to a coding sequence;
    (ii) the coding sequence encodes a RNA transcription product;
  (b) transcribing a RNA transcription product from the coding sequence in a complex present after (a), wherein the RNA transcription product comprises a compomer consisting of one, two or three nucleotide types, and a terminal nucleotide sequence consisting of one or more nucleotide types not included in the compomer;
  (c) cleaving the RNA transcription product thereby generating a cleavage product, wherein the 3' terminus of the compomer is at the 3' terminus of the cleavage product; and
  (d) detecting the presence or absence of the cleavage product that includes the compomer, whereby the presence or absence of the target nucleic acid is identified based on the presence or absence of the cleavage product.

2. The method of claim 1, wherein the cleavage product consists of the compomer.

3. The method of claim 1, wherein the RNA transcription product consists of the compomer and a terminal nucleotide sequence common to one or more other RNA transcription products.

4. The method of claim 3, wherein the nucleotides in the compomer and terminal nucleotide sequence are selected from the group consisting of adenine (A), thymine (T), guanine (G), and cytosine (C).

5. The method of claim 1, wherein the RNA transcription product consists of the compomer and the presence or absence of the compomer is identified without cleaving the RNA transcription product.

6. The method of claim 1, wherein the presence or absence of the cleavage product is identified by mass spectrometry.

7. The method of claim 5, wherein the presence or absence of the cleavage product is identified in a mass range of about 2500 Daltons and about 10000 Daltons.

8. The method of claim 1, wherein the RNA transcription product is cleaved by a process selected from the group consisting of a chemical, a physical, and an enzymatic process.

9. The method of claim 1, wherein the promoter region is selected from the group consisting of a bacterial, a bacteriophage, a consensus, a viral and a eukaryotic promoter region.

10. The method of claim 1, wherein the promoter region is a bacteriophage promoter region selected from the group consisting of a T7, an SP6, and a T3 promoter region.

11. The method of claim 1, wherein the target nucleic acid is selected from the group consisting of a source of genetic variation among members of the same species and a chemically modified nucleic acid molecule.

12. The method of claim 1, wherein the target detection reagent is one of a plurality of target detection reagents, and wherein RNA transcription product comprises a unique compomer species.

* * * * *